United States Patent [19]
Oku et al.

[11] Patent Number: 6,015,818
[45] Date of Patent: Jan. 18, 2000

[54] QUINOLINE DERIVATIVES AS BRADYKININ AGONISTS

[75] Inventors: Teruo Oku; Hiroshi Kayakiri, both of Tsukuba; Yoshito Abe, Inashiki-gun; Yuki Sawada; Tsuyoshi Mizutani, both of Tsukuba, all of Japan

[73] Assignee: Fujisawa Pharmaceutical Co., Ltd., Osaka, Japan

[21] Appl. No.: 09/117,453

[22] PCT Filed: Jan. 31, 1997

[86] PCT No.: PCT/JP97/00233

§ 371 Date: Aug. 3, 1998

§ 102(e) Date: Aug. 3, 1998

[87] PCT Pub. No.: WO97/28153

PCT Pub. Date: Aug. 7, 1997

[30] Foreign Application Priority Data

Feb. 1, 1996 [GB] United Kingdom ................... 96-02029

[51] Int. Cl.[7] ..................... C07D 401/12; C07D 401/14; A61K 31/395
[52] U.S. Cl. .............................. 514/312; 546/153
[58] Field of Search ............................. 546/153; 514/312

[56] References Cited

U.S. PATENT DOCUMENTS

| | | | |
|---|---|---|---|
| 5,563,162 | 10/1996 | Oku et al. | 514/311 |
| 5,574,042 | 11/1996 | Oku et al. | 514/300 |
| 5,708,173 | 1/1998 | Oku et al. | 546/153 |
| 5,750,699 | 5/1998 | Oku et al. | 546/121 |

FOREIGN PATENT DOCUMENTS 622361  11/1994  European Pat. Off. .

*Primary Examiner*—Mukund J. Shah
*Assistant Examiner*—Deepak R. Rao
*Attorney, Agent, or Firm*—Oblon, Spivak, McClelland, Maier & Neustadt, P.C.

[57] ABSTRACT

This invention relates to a compound of formula (1) wherein $R^1$ is halogen, etc., $R^2$ is halogen, etc., $R^3$ is amino substituted with substituent(s) selected from the group consisting of lower alkyl and acyl, etc., $R^4$ is heterocyclic (lower)alkyl, $R^5$ is lower alkyl, and $A^1$ is lower alkylene, and pharmaceutically acceptable salts thereof, to processes for preparation thereof, to a pharmaceutical composition comprising the same, and to methods of using the same therapeutically in the prevention and/or the treatment of hypertension or the like.

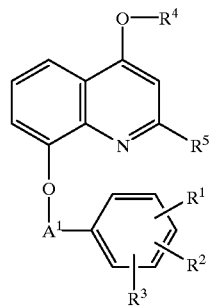

9 Claims, No Drawings

QUINOLINE DERIVATIVES AS BRADYKININ AGONISTS

This application is a 371 of PCT/JP97/00233 filed on Jan. 31, 1997.

1. Technical Field

This invention relates to new heterocyclic compounds and pharmaceutically acceptable salts thereof.

More particularly, it relates to new heterocyclic compounds and pharmaceutically acceptable salts thereof which have activities as bradykinin agonists, to processes for preparation thereof, to a pharmaceutical composition comprising the same, and to methods of using the same for the therapeutic purpose in human being or animals.

One object of this invention is to provide new and useful heterocyclic compounds and pharmaceutically acceptable salts thereof which possess activities as bradykinin agonists.

Another object of this invention is to provide processes for the preparation of said compounds and salts thereof.

A further object of this invention is to provide a pharmaceutical composition comprising, as an active ingredient, said heterocyclic compounds and pharmaceutically acceptable salts thereof.

2. Background Art

Heterocyclic compounds having activities as bradykinin antagonists have been known as described in EP-A-596,406, EP-A-622,36, WO96/04251 and WO96/13485. However, it is not known that said compounds have activities as bradykinin agonists.

Disclosure of the Invention

The object heterocyclic compounds of this invention are new and can be represented by the following general formula [I]:

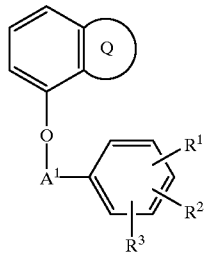

wherein

is a group of the formula:

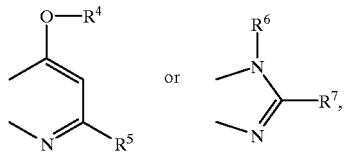

in which
R$^4$ is heterocyclic(lower)alkyl,
R$^5$ is lower alkyl,
R$^6$ is acyl(lower)alkyl, ar(lower)alkyl or heterocyclic (lower)alkyl, and
R$^7$ is lower alkyl or lower alkoxy, R$^1$ is hydrogen, lower alkyl or halogen, R$^2$ is lower alkyl or halogen, R$^3$ is amino substituted with substituent(s) selected from the group consisting of lower alkyl and acyl, or a group of the formula:

—Z—A$^2$R$^{11}$, in which

R$^{11}$ is amino or acylamino,

A$^2$ is lower alkylene or a single bond, and

Z is lower alkenylene or a group of the formula:

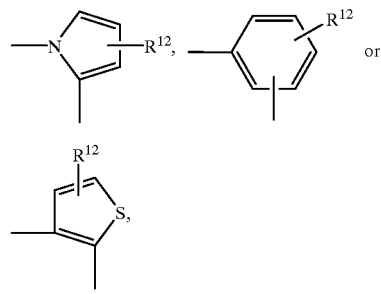

in which

R$^{12}$ is hydrogen or halogen, and

A$^1$ is lower alkylene.

The object compound [I] or its salt can be prepared by processes as illustrated in the following reaction schemes.

Process 1

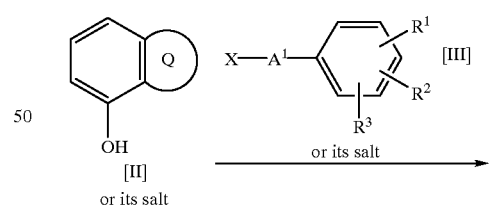

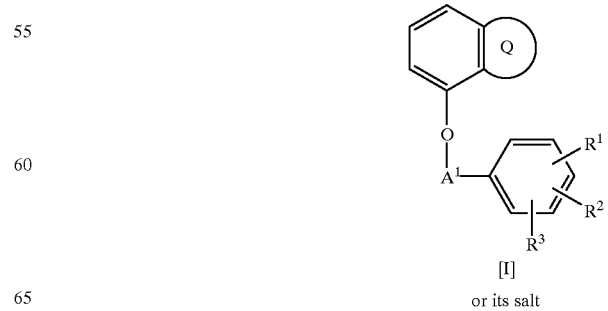

Process 2

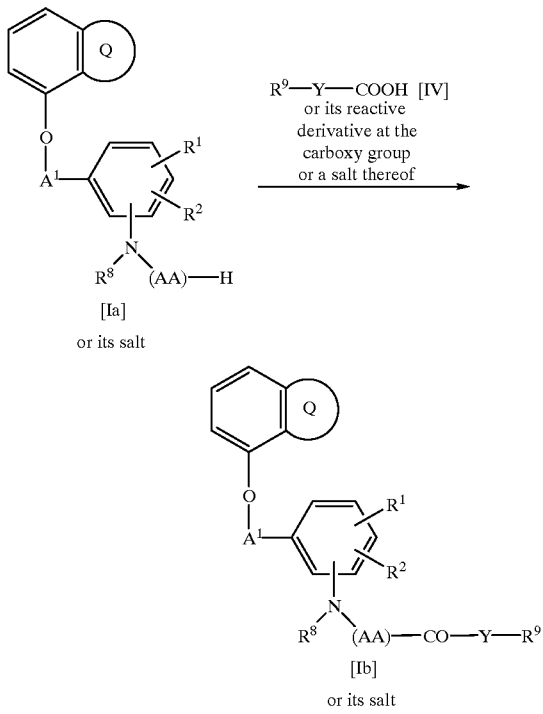

wherein $R^8$ is hydrogen or lower alkyl,
$R^9$ is aryl or a heterocyclic group, each of which may be substituted with substituent(s) selected from the group consisting of amino, acyl, acylamino, lower alkyl, lower alkoxy, heterocyclic(lower)alkenyl and a heterocyclic group optionally substituted with oxo,
(AA) is amino acid residue,
X is a leaving group,
Y is lower alkenylene or NH, and
$R^1$, $R^2$, $R^3$, $A^1$ and

are each as defined above.

In the above and subsequent description of the present specification, suitable examples of the various definitions to be included within the scope of the invention are explained in detail in the following.

The term "flower" is intended to mean a group having 1 to 6 carbon atom(s), unless otherwise provided.

In this respect, the term "lower" in lower alkenyl moieties in the various definitions is intended to mean a group having 2 to 6 carbon atoms.

Further, the term "lower" in ar(lower)alkenoyl moiety and heterocyclic(lower)alkenoyl moiety in the various definitions is intended to mean a group having 3 to 6 carbon atoms.

Suitable "lower alkyl" and lower alkyl moiety such as in the terms "heterocyclic(lower)alkyl", "acyl(lower)alkyl", etc., may be straight or branched one such as methyl, ethyl, propyl, isopropyl, butyl, isobutyl, tert-butyl, pentyl, hexyl or the like, in which preferable one is $C_1$–$C_4$ alkyl such as methyl, ethyl, propyl, isobutyl or tert-butyl.

Suitable "lower alkoxy" may be straight or branched one such as methoxy, ethoxy, propoxy, isopropoxy, butoxy, isobutoxy, tert-butoxy, pentyloxy, hexyloxy or the like, in which preferable one is $C_1$–$C_4$ alkoxy such as methoxy, ethoxy or isopropoxy.

Suitable lower alkenyl moiety in the term "heterocyclic (lower)alkenyl" may be a straight or branched one such as vinyl, allyl, 1-propenyl, isopropenyl, butenyl, isobutenyl, pentenyl, hexenyl or the like.

Suitable "halogen" may be fluorine, chlorine, bromine and iodine.

Suitable "acyl" and acyl moiety in the terms "acylamino" and "acyl(lower)alkyl" may be substituted or unsubstituted alkanoyl such as alkanoyl [e.g. formyl, acetyl, propionyl, butyryl, isobutyryl, valeryl, isovaleryl, pivaloyl, hexanoyl, heptanoyl, 3,3-dimethylbutyryl, etc.], halo(lower)alkanoyl [e.g. chloroacetyl, trifluoroacetyl, bromoacetyl, bromobutyryl, heptafluorobutyryl, etc.], hydroxy(lower) alkanoyl [e.g. glycoloyl, lactoyl, 3-hydroxypropionyl, glyceroyl, etc.], lower alkylsulfonyloxy(lower)alkanoyl [e.g. mesyloxyacetyl, ethylsulfonyloxyacetyl, mesyloxypropionyl, etc.], lower alkoxy(lower)alkanoyl [e.g. methoxyacetyl, ethoxyacetyl, methoxypropionyl, ethoxypropionyl, propoxypropionyl, methoxybutyryl, etc.], lower alkylthio(lower)alkanoyl [e.g. methylthioacetyl, ethylthioacetyl, methylthiopropionyl, ethylthiopropionyl, propylthiopropionyl, methylthiobutyryl, etc.], lower alkanoyloxy(lower)alkanoyl [e.g. acetyloxyacetyl, acetyloxypropionyl, propionyloxyacetyl, etc.], aryloxy (lower)alkanoyl [e.g. phenyloxyacetyl, phenyloxypropionyl, tolyloxyacetyl, naphthyloxyacetyl, etc.], aroyl(lower) alkanoyl [e.g. phenyloxalyl, benzoylacetyl, benzoylpropionyl, etc.], carboxy(lower)alkanoyl [e.g. oxalo, carboxyacetyl, 3-carboxypropionyl, 3-carboxybutyryl, 4-carboxybutyryl, 4-carboxyvaleryl, etc.], esterified carboxy (lower)alkanoyl, for example, lower alkoxycarbonyl(lower) alkanoyl [e.g. methoxycarbonylacetyl, ethoxycarbonylacetyl, methoxycarbonylpropionyl, ethoxycarbonylpropionyl, etc.], carbamoyl(lower)alkanoyl [e.g. carbamoylacetyl, carbamoylpropionyl, etc.], lower alkylcarbamoyl(lower)alkanoyl [e.g. methylcarbamoylacetyl, methylcarbamoylpropionyl, ethylcarbamoylpropionyl, dimethylcarbamoylpropionyl, (N-methyl-N-ethylcarbamoyl)-propionyl, etc.], ar(lower) alkanoyl [e.g. phenylacetyl, tolylacetyl, naphthylacetyl, 2-phenylpropionyl, 3-phenylpropionyl, 4-phenylbutyryl, tritylcarbonyl, etc.], heterocyclic(lower) alkylcarbamoyl-ar (lower)alkanoyl [e.g. pyridylmethylcarbamoylphenylpropionyl, furylmethylcarbamoylphenylpropionyl, etc.], optionally substituted heterocyclic(lower)alkanoyl [e.g. morpholinoacetyl, thiomorpholinoacetyl, morpholinopropionyl, thiomorpholinopropionyl, piperidinopropionyl, piperazinylpropionyl, pyridylacetyl, pyrrolidinylpropionyl, imidazolidinylpropionyl, piperidinoacetyl, pyrrolidinylacetyl, hexamethyleneiminoacetyl, hexamethyleneiminopropionyl, imidazolylacetyl, furylacetyl, thienylacetyl, nethylpiperazinylacetyl, pyridylpiperazinylacetyl, etc.], heterocyclicthio(lower) alkanoyl [e.g. pyridylthioacetyl, pyrimidinylthioacetyl, imidazolylthiopropionyl, etc.], etc., lower alkenoyl [e.g. acryloyl, crotonoyl, isocrotonoyl, 3-butenoyl, 3-pentenoyl, 4-pentenoyl, methacryloyl, etc.], lower alkynoyl [e.g. propioloyl, 2-butynoyl, 3-butynoyl, etc.], cyclo(lower)alkylcarbonyl [e.g. cyclopropylcarbonyl, cyclobutylcarbonyl, cyclopentylcarbonyl, cyclohexylcarbonyl, etc.], cyclo(lower)alkenylcarbonyl [e.g. cyclopentenylcarbonyl, cyclohexenylcarbonyl, etc.], carboxy, esterified carboxy such as lower alkoxycarbonyl

[e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], aryloxycarbonyl [e.g. phenoxycarbonyl, etc.], etc., substituted or unsubstituted aroyl such as aroyl [e.g. benzoyl, toluoyl, xyloyl, naphthoyl, etc.], lower alkoxyaroyl [e.g. methoxybenzoyl, etc.], haloaroyl [e.g. chlorobenzoyl, fluorobenzoyl, etc.], acylaroyl, for example, lower alkoxycarbonylaroyl [e.g. methoxycarbonylbenzoyl, etc.], etc., substituted or unsubstituted ar(lower)alkenoyl such as ar(lower)alkenoyl [e.g. cinnamoyl, allocinnamoyl, α-methylcinnamoyl, 4-methylcinnamoyl, etc.], lower alkoxy-ar(lower)alkenoyl [e.g. methoxycinnamoyl, ethoxycinnamoyl, dimethoxycinnamoyl, etc.], lower alkylenedioxy-ar(lower)alkenoyl [e.g. methylenedioxycinnamoyl, ethylenedioxycinnamoyl, etc.], nitro-ar(lower)alkenoyl [e.g. nitrocinnamoyl, etc.], cyano-ar(lower)alkenoyl [e.g. cyanocinnamoyl, etc.], halo-ar(lower)alkenoyl [e.g. chlorocinnamoyl, fluorocinnamoyl, etc.], hydroxy-ar(lower)alkenoyl [e.g. hydroxycinnamoyl, etc.], hydroxy(lower)alkoxy-ar(lower)alkenoyl [e.g. hydroxymethoxycinnamoyl, hydroxyethoxycinnamoyl, etc.], amino(lower)alkoxy-ar(lower)alkenoyl [e.g. aminoethoxycinnamoyl, etc.], lower alkylamino(lower)-alkoxy-ar(lower)alkenoyl [e.g. methylaminomethoxycinnamoyl, dimethylaminoethoxycinnamoyl, etc.], heterocyclic(lower)alkoxy-ar(lower)alkenoyl [e.g. pyridylmethoxycinnamoyl, etc.], optionally substituted heterocyclic-ar(lower)alkenoyl [e.g. morpholinocinnamoyl, methylpiperazinylcinnamoyl, pyrrolidinylcinnamoyl, oxopyrrolidinylcinnamoyl, oxopiperidinocinnamoyl, dioxopyrrolidinylcinnamoyl, oxooxazolidinylcinnamoyl, pyrrolylcinnamoyl, tetrazolylcinnamoyl, etc.], heterocyclic(lower)alkyl-ar(lower)alkenoyl[e.g. pyridylmethylcinnamoyl, pyridylethylcinnamoyl, quinolylethylcinnamoyl, etc.], heterocyclic(lower)alkenyl-ar(lower)alkenoyl [e.g. pyridylvinylcinnamoyl, quinolylvinylcinnamoyl, etc.], amino-ar(lower)alkenoyl [e.g. aminocinnamoyl, etc.], lower alkylamino-ar(lower)alkenoyl [e.g. methylaminocinnamoyl, dimethylaminocinnamoyl, etc.], acylamino-ar(lower) alkenoyl, for example, lower alkanoylamino-ar(lower) alkenoyl [e.g. acetylaminocinnamoyl, propionylaminocinnamoyl, isobutyrylaminocinnamoyl, 4-acetylamino-3-methylcinnamoyl, etc.], cycloalkyl(lower) alkanoylamino-ar(lower)alkenoyl [e.g. cyclopentylacetylaminocinnamoyl, cyclohexylacetylaminocinnamoyl, adamantylacetylaminocinnamoyl, etc.], cycloalkylcarbonylamino-ar(lower)alkenoyl [e.g. cyclopropylcarbonylaminocinnamoyl, cyclopentylcarbonylaminocinnamoyl, cyclohexylcarbonylaminocinnamoyl, adamantylcarbonylaminocinnamoyl, etc.], lower alkenoylamino-ar(lower)alkenoyl [e.g. acryloylaminocinnamoyl, crotonoylaminocinnamoyl, etc.], lower alkoxycarbonylamino-ar(lower)alkenoyl [e.g. methoxycarbonylaminocinnamoyl, ethoxycarbonylaminocinnamoyl, etc.], hydroxy(lower) alkanoylamino-ar(lower)alkenoyl [e.g. hydroxyacetylaminocinnamoyl, hydroxypropionylaminocinnamoyl, etc.], lower alkoxy (lower)alkanoylamino-ar(lower)alkenoyl [e.g. methoxyacetylaminocinnamoyl, methoxypropionylaminocinnamoyl, etc.], halo(lower) alkanoylamino-ar(lower)alkenoyl [e.g. chloroacetylaminocinnamoyl, bromobutyrylaminocinnamoyl, trifluoroacetylaminocinnamoyl, etc.], amino(lower) alkanoylamino-ar(lower)alkenoyl [e.g. aminoacetylaminocinnamoyl, aminopropionylaminocinnamoyl, etc.], lower alkylamino (lower)alkanoylamino-ar(lower)-alkenoyl [e.g. methylaminoacetylaminocinnamoyl, dimethylaminoacetylaminocinnamoyl, etc.], lower alkanoylamino(lower)alkanoylamino-ar(lower)alkenoyl [e.g. acetylaminoacetylaminocinnamoyl, acetylaminopropionylaminocinnamoyl, etc.], carboxy (lower)alkanoylamino-ar(lower)alkenoyl [e.g. carboxyacetylaminocinnamoyl, carboxypropionylaminocinnamoyl, etc.], lower alkoxycarbonyl(lower)alkanoylamino-ar(lower)alkenoyl [e.g. ethoxycarbonylacetylaminocinnamoyl, ethoxycarbonylpropionylaminocinnamoyl, etc.], lower alkoxycarbonyl(lower)alkenoylamino-ar(lower)alkenoyl [e.g. ethoxycarbonylacryloylaminocinnamoyl, etc.], halo (lower)alkoxycarbonylamino-ar(lower)alkenoyl [e.g. chloroethoxycarbonylaminocinnamoyl, etc.], optionally substituted heterocyclic(lower)alkanoylamino-ar(lower)-alkenoyl [e.g. pyridylacetylaminocinnamoyl, thienylacetylaminocinnamoyl, methylpyrrolylacetylaminocinnamoyl, etc.], aroylamino-ar (lower)alkenoyl [e.g. benzoylaminocinnamoyl, etc.], optionally substituted heterocycliccarbonylamino-ar(lower) alkenoyl [e.g. pyridylcarbonylaminocinnamoyl, morpholinocarbonylaminocinnamoyl, furylcarbonylaminocinnamoyl, thienylcarbonylaminocinnamoyl, oxazolylcarbonylaminocinnamoyl, methyloxazolylcarbonylaminocinnamoyl, dimethylisoxazolylcarbonylaminocinnamoyl, imidazolylcarbonylaminocinnamoyl, methylimidazolylcarbonylaminocinnamoyl, piperidylcarbonylaminocinnamoyl, ethylpiperidylcarbonylaminocinnamoyl, acetylpiperidylcarbonylaminocinnamoyl, pyrrolidinylcarbonylaminocinnamoyl acetylpyrrolidinylcarbonylaminocinnamoyl, tert-butoxycarbonylpyrrolidinylcarbonylaminocinnamoyl, etc.], lower alkylsulfonylamino-ar(lower)alkenoyl [e.g. mesylaminocinnamoyl, ethylsulfonylaminocinnamoyl, etc.], etc., N-(lower alkanoyl)-N-(lower alkyl)amino-ar (lower)alkenoyl [e.g. N-acetyl-N-methylaminocinnamoyl, N-acetyl-N-ethylaminocinnamoyl, N-propionyl-N-methylaminocinnamoyl, etc.], N-[lower alkoxy(lower) alkanoyl ]-N-(lower alkyl)amino-ar(lower)alkenoyl [e.g. N-methoxyacetyl-N-methylaminocinnamoyl, N-methoxypropionyl-N-methylaminocinnamoyl, etc.], N-(lower alkanoyl)-N-heterocyclic(lower)alkyliamino-ar (lower)alkenoyl [e.g. N-acetyl-N-pyridylmethylamino-cinnamoyl, etc.], N-(lower alkanoyl)-N-[lower alkoxy (lower)alkyl]amino-ar(lower)alkenoyl [e.g. N-acetyl-N-methoxyethylaminocinnamoyl, N-acetyl-N-methoxymethylaminocinnamoyl, N-propionyl-N-methoxyethylaminocinnamoyl, etc.], N-(lower alkanoyl)-N-[lower alkoxycarbonyl(lower)alkyl]-amino-ar(lower) alkenoyl [e.g. N-acetyl-N-tert-butoxycarbonylmethylaminocinnamoyl, N-acetyl-N-tert-butoxycarbonylethylaminocinnamoyl, N-propionyl-N-tert-butoxycarbonylmethylaminocinnamoyl, etc.], N-(lower alkanoyl)-N-[carboxy(lower)alkyl]amino-ar(lower)alkenoyl [e.g. N-acetyl-N-carboxymethylaminocinnamoyl, N-acetyl-N-carboxyethylaminocinnamoyl, N-propionyl-N-carboxymethylaminocinnamoyl, etc.], N-[lower alkoxy (lower)alkanoyl]-N-[heterocyclic(lower)alkyl]amino-ar (lower)alkenoyl [e.g. N-methoxyacetyl-N-pyridylmethylaminocinnamoyl, N-methoxypropionyl-N-pyridylmethylaminocinnamoyl, etc.], N-[heterocycliccarbonyl]-N-[lower alkoxy(lower)alkyl] amino-ar(lower)alkenoyl [e.g. N-pyridylcarbonyl-N-methoxymethylaminocinnamoyl, N-pyridylcarbonyl-N-methoxyethylaminocinnamoyl, N-thienylcarbonyl-N-methoxyethylaminocinnamoyl, etc.], ureido-ar(lower) alkenoyl [e.g. ureidocinnamoyl, etc.], lower alkylureido-ar (lower)alkenoyl [e.g. methylureidocinnamoyl, ethylureidocinnamoyl, dimethylureidocinnamoyl, etc.], heterocyclicureido-ar(lower)alkenoyl [e.g. pyridylureidocinnamoyl, pyrimidinylureidocinnamoyl, thienylureidocinnamoyl, etc.], acyl-ar(lower)alkenoyl, for example, lower alkanoyl-ar(lower)alkenoyl [e.g. formylcinnamoyl, acetylcinnamoyl, propionylcinnamoyl, etc.], carboxy-ar(lower)alkenoyl [e.g. carboxycinnamoyl, etc.], lower alkoxycarbonyl-ar(lower)alkenoyl [e.g. methoxycarbonylcinnamoyl, ethoxycarbonylcinnamoyl, etc.], carbamoyl-ar(lower)alkenoyl [e.g. carbamoylcinnamoyl, etc.], lower alkylcarbamoyl-ar(lower) alkenoyl [e.g. methylcarbamoylcinnamoyl, ethylcarbamoylcinnamoyl, dimethylcarbamoylcinnamoyl, propylcarbamoylcinnamoyl, isopropylcarbamoylcinnamoyl, diethylcarbamoylcinnamoyl, N-methyl-N-ethylcarbamoylcinnamoyl, etc.], (lower alkylcarbamoyl) (lower alkoxy)-ar(lower)alkenoyl [e.g. 4-methylcarbamoyl-3-methoxycinnamoyl, 4-dimethylcarbamoyl-3-methoxycinnamoyl, etc.], hydroxy(lower)alkylcarbamoyl-ar (lower)alkenoyl [e.g. hydroxyethylcarbamoylcinnamoyl, bis (hydroxyethyl)carbamoylcinnamoyl, etc.], N-[hydroxy (lower)alkyl]-N-(lower alkyl)carbamoyl-ar(lower)alkenoyl [e.g. N-hydroxyethyl-N-methylcarbamoylcinnamoyl, etc.], lower alkoxy(lower)alkylcarbamoyl-ar(lower)alkenoyl [e.g. methoxymethylcarbamoylcinnamoyl, methoxyethylcarbamoylcinnamoyl, bis (methoxyethyl) carbamoyicinnamoyl, ethoxyethylcarbamoylcinnamoyl, methoxypropylcarbamoylcinnamoyl, bis(ethoxyethyl) carbamoylcinnamoyl, etc.], N-[lower alkoxy(lower)alkyl]-N-(lower alkyl)carbamoyl-ar(lower)alkenoyl [e.g. N-methoxyethyl-N-methylcarbamoylcinnamoyl, N-ethoxyethyl-N-methylcarbamoylcinnamoyl, etc.], heterocyclic(lower)alkylcarbamoyl-ar(lower)alkenoyl [e.g. pyridylmethylcarbamoylcinnamoyl, furylmethylcarbamoylcinnamoyl, thienylmethylcarbamoylcinnamoyl, etc.], N-[heterocyclic (lower)alkyl]-N-(lower alkyl)carbamoyl-ar(lower)alkenoyl [e.g. N-pyridylmethyl-N-methylcarbamoylcinnamoyl, etc.], heterocycliccarbamoyl-ar(lower)alkenoyl [e.g. morpholinylcarbamoylcinnamoyl, thienylcarbamoylcinnamoyl, pyridylcarbamoylcinnamoyl, pyrimidinylcarbamoylcinnamoyl, tetrazolylcarbamoylcinnamoyl, etc.], optionally substituted heterocycliccarbonyl-ar(lower)alkenoyl [e.g. morpholinocarbonylcinnamoyl, pyrrolidinylcarbonylcinnamoyl, piperidinocarbonylcinnamoyl, tetrahydropyridylcarbonylcinnamoyl, methylpiperazinylcarbonylcinnamoyl, etc.], lower alkenylcarbamoyl-ar(lower)alkenoyl [e.g. vinylcarbamoylcinnamoyl, allylcarbamoylcinnamoyl, methylpropenylcarbamoylcinnamoyl, etc.], lower alkynylcarbamoyl-ar(lower)alkenoyl [e.g. ethynylcarbamoylcinnamoyl, propynylcarbamoylcinnamoyl, etc.], amino(lower) alkylcarbamoyl-ar(lower)alkenoyl [e.g. aminomethylcarbamoylcinnamoyl, aminoethylcarbamoylcinnamoyl, etc.], lower alkylamino (lower)alkylcarbamoyl-ar(lower)alkenoyl [e.g. methylaminomethylcarbamoylcinnamoyl, methylaminoethylcarbamoylcinnamoyl, ethylaminoethylcarbamoylcinnamoyl, dimethylaminoethylcarbamoylcinnamoyl, etc.], lower alkylcarbamoyloxy(lower)alkylcarbamoyl-ar(lower) alkenoyl [e.g. methylcarbamoyloxymethylcarbamoylcinnamoyl, methylcarbamoyloxyethylcarbamoylcinnamoyl, ethylcarbamoyloxyethylcarbamoylcinnamoyl, dimethylcarbamoyloxyethylcarbamoylcinnamoyl, etc.], lower alkylcarbamoyl(lower)alkylcarbamoyl-ar(lower) alkenoyl [e.g. methylcarbamoylmethylcarbamoylcinnamoyl, methylcarbamoylethylcarbamoylcinnamoyl, ethylcarbamoylethylcarbamoylcinnamoyl, dimethylcarbamoylethylcarbamoylcinnamoyl, etc.], lower alkoxycarbonyl(lower)alkylcarbamoyl-ar(lower)alkenoyl [e.g. methoxycarbonylmethylcarbamoylcinnamoyl, methoxycarbonylethylcarbamoylcinnamoyl, ethoxycarbonylmethylcarbamoylcinnamoyl, ethoxycarbonylethylcarbamoylcinnamoyl, etc.], carboxy (lower)alkylcarbamoyl-ar(lower)alkenoyl [e.g. carboxymethylcarbamoylcinnamoyl, carboxyethylcarbamoylcinnamoyl, etc.], [lower alkylcarbamoyl-ar(lower)alkyl]carbamoyl-ar(lower) alkenoyl [e.g. (methylcarbamoyl-phenethyl) carbamoylcinnamoyl, (ethylcarbamoyl-phenethyl) carbamoylcinnamoyl, etc.], [lower alkoxycarbonyl-ar (lower)alkyl]carbamoyl-ar(lower)alkenoyl [e.g. (methoxycarbonyl-phenethyl)-carbamoylcinnamoyl, (ethoxycarbonyl-phenethyl)-carbamoylcinnamoyl, etc.], [carboxy-ar(lower)alkyl]carbamoyl-ar(lower)alkenoyl [e.g. carboxy-phenethyl)carbamoylcinnamoyl, etc.], N-[lower alkylcarbamoyl(lower)alkyl]-N-(lower alkyl)carbamoyl-ar (lower)alkenoyl [e.g. N-(methylcarbamoylmethyl)-N-methylcarbamoylcinnamoyl, N-(methylcarbamoylethyl)-N-methylcarbamoylcinnamoyl, N-(ethylcarbamoylethyl)-N-methylcarbamoylcinnamoyl, N-(dimethylcarbamoylethyl)-N-methylcarbamoylcinnamoyl, etc.], N-[lower alkoxycarbonyl(lower)alkyl]-N-(lower alkyl)carbamoyl-ar (lower)alkenoyl [e.g. N-methoxycarbonylmethyl-N-methylcarbamoylcinnamoyl, N-methoxycarbonylethyl-N-methylcarbamoylcinnamoyl, N-ethoxycarbonylmethyl-N-methylcarbamoylcinnamoyl, N-ethoxycarbonylethyl-N-methylcarbamoylcinnamoyl, etc.], N-[carboxy(lower) alkyl]-N-(lower alkyl)carbamoyl-ar(lower)alkenoyl [e.g. N-carboxymethyl-N-methylcarbamoylcinnamoyl, N-carboxyethyl-N-methylcarbamoylcinnamoyl, etc.], arylcarbamoyl-ar(lower)alkenoyl [e.g. phenylcarbamoylcinnamoyl, naphthylcarbamoylcinnamoyl, etc.], etc., etc., ar(lower)alkynoyl [e.g. phenylpropioloyl, etc.], substituted or unsubstituted heterocyclic(lower) alkenoyl such as heterocyclic(lower)alkenoyl [e.g. morpholinylacryloyl, pyridylacryloyl, thienylacryloyl, etc.], heterocyclic(lower)alkyl-heterocyclic(lower)alkenoyl [e.g. pyridylmethylpyridylacryloyl, pyridylethylpyridylacryloyl, quinolylethylpyridylacryloyl, etc.], heterocyclic(lower) alkenyl-heterocyclic(lower)-alkenoyl [e.g. pyridylvinylpyridylacryloyl, quinolylvinylpyridylacryloyl, etc.], amino-heterocyclic(lower)alkenoyl [e.g. aminopyridylacryloyl, etc.], lower alkylamino-heterocyclic (lower)alkenoyl [e.g. methylaminopyridylacryloyl, dimethylaminopyridylacryloyl, etc.], acylamino-heterocyclic(lower)alkenoyl, for example, lower alkanoylamino-heterocyclic(lower)alkenoyl [e.g. acetylaminopyridylacryloyl, propionylaminopyridylacryloyl, etc.], lower alkenoylamino-heterocyclic(lower)alkenoyl [e.g. acryloylaminopyridylacryloyl, crotonoylaminopyridylacryloyl, etc.], heterocyclic(lower)alkanoylamino-heterocyclic(lower)-alkenoyl [e.g. pyridylacetylaminopyridylacryloyl, thienylacetylaminopyridylacryloyl, etc.], optionally substituted heterocycliccarbonylamino-heterocyclic(lower) alkenoyl [e.g. pyridylcarbonylaminopyridylacryloyl, furylcarbonylaminopyridylacryloyl, methylpyridylcarbonylaminopyridylacryloyl, etc.], lower alkanoylamino(lower)alkanoylamino-heterocyclic(lower)-alkenoyl [e.g. acetylaminoacetylaminopyridylacryloyl, acetylaminopropionylaminopyridylacryloyl, etc.], lower alkoxycarbonyl(lower)alkanoylamino-heterocyclic(lower)-alkenoyl [e.g. ethoxycarbonylacetylaminopyridylacryloyl, ethoxycarbonylpropionylaminopyridylacryloyl, etc.], lower alkoxy(lower)alkanoylamino-heterocyclic(lower)alkenoyl [e.g. methoxyacetylaminopyridylacryloyl, methoxypropionyl-aminopyridylacryloyl, ethoxypropionylaminopyridylacryloyl, etc.], etc., lower alkylureido-heterocyclic(lower)alkenoyl [e.g. methylureidopyridylacryloyl, etc.], acyl-heterocyclic(lower)alkenoyl, for example, carboxy-heterocyclic(lower)alkenoyl [e.g. carboxypyridylacryloyl, etc.], lower alkoxycarbonyl-heterocyclic(lower)alkenoyl [e.g. ethoxycarbonylpyridylacryloyl, etc.], lower alkanoyl-heterocyclic(lower)alkenoyl [e.g. acetyl-pyridylacryloyl, acetyltetrahydroquinolylacryloyl, etc.], lower alkylcarbamoyl-heterocyclic(lower)alkenoyl [e.g. methylcarbamoylpyridylacryloyl, ethylcarbamoylpyridylacryloyl, dimethylcarbamoylpyridylacryloyl, diethylcarbamoylpyridylacryloyl, isopropylcarbamoylpyridylacryloyl, N-ethyl-N-methylcarbamoylpyridylacryloyl, etc.], lower alkoxy(lower)alkylcarbamoyl-heterocyclic(lower)alkenoyl [e.g. methoxymethylcarbamoylpyridylacryloyl, methoxyethylcarbamoylpyridylacryloyl, methoxypropylcarbamoylpyridylacryloyl, ethoxyethylcarbamoylpyridylacryloyl, bis (ethoxyethyl) carbamoylpyridylacryloyl, etc.], hydroxy(lower)alkylcarbamoyl-heterocyclic(lower)alkenoyl [e.g. hydroxymethylcarbamoylpyridylacryloyl, hydroxyethylcarbamoylpyridylacryloyl, bis(hydroxyethyl) carbamoylpyridylacryloyl, etc.], heterocycliccarbamoyl-heterocyclic(lower)alkenoyl [e.g. pyridylcarbamoylpyridylacryloyl, morpholinylcarbamoylpyridylacryloyl, thienylcarbamoylpyridylacryloyl, pyrimidinylcarbamoylpyridylacryloyl, etc.], heterocyclic(lower)alkylcarbamoyl-heterocyclic(lower)-alkenoyl [e.g. pyridylmethylcarbamoylpyridylacryloyl, furylmethylcarbamoylpyridylacryloyl, thienylmethylcarbamoylpyridylacryloyl, etc.], heterocycliccarbonyl-heterocyclic(lower)alkenoyl [e.g. morpholinocarbonylpyridylacryloyl, pyrrolidinylcarbonylpyridylacryloyl, piperidinocarbonylpyridylacryloyl, etc.], lower alkenylcarbamoyl-heterocyclic(lower)alkenoyl [e.g. vinylcarbamoylpyridylacryloyl, allylcarbamoylpyridylacryloyl, etc.], lower alkynylcarbamoyl-heterocyclic(lower)alkenoyl [e.g. ethynylcarbamoylpyridylacryloyl, propynylcarbamoylpyridylacryloyl, etc.], etc., hetero-cycliccarbonyl which may be substituted with substituent [e.g. furoyl, thenoyl, nicotinoyl, methylnicotinoyl, isonicotinoyl, morpholinocarbonyl, piperidinocarbonyl, 4-methyl-1-piperazinylcarbonyl, 4-ethyl-1-piperazinylcarbonyl, dimethylaminopiperidinocarbonyl, 4-methylcarbamoyl-1-piperazinylcarbonyl, 1,2,3,6-tetrahydropyridylcarbonyl, pyrrolidinylcarbonyl, indolylcarbonyl, etc.], aryloxycarbonyl which may be substituted with nitro [e.g. phenyloxycarbonyl, nitrophenyloxycarbonyl, etc.], ar(lower)alkoxycarbonyl which may be substituted with nitro [e.g. benzyloxycarbonyl, nitrobenzyloxycarbonyl, etc.], substituted or unsubstituted carbamoyl or thiocarbamoyl such as carbamoyl, lower alkylcarbamoyl [e.g. methylcarbamoyl, ethylcarbamoyl, propylcarbamoyl, isopropylcarbamoyl, butylcarbamoyl, isobutylcarbamoyl, tert-butylcarbamoyl, pentylcarbamoyl, dimethylcarbamoyl, diethylcarbamoyl, N-ethyl-N-methylcarbamoyl, etc.], carboxy(lower) alkylcarbamoyl [e.g. carboxymethylcarbamoyl, carboxyethylcarbamoyl, etc.], esterified carboxy(lower) alkylcarbamoyl, for example, lower alkoxycarbonyl(lower) alkylcarbamoyl [e.g. methoxycarbonylmethylcarbamoyl, ethoxycarbonylmethylcarbamoyl, ethoxycarbonylethylcarbamoyl, etc.], lower alkenylcarbamoyl [e.g. vinylcarbamoyl, allylcarbamoyl, etc.], cyclo(lower) alkylcarbamoyl [e.g. cyclopropylcarbamoyl, cyclobutylcarbamoyl, cyclopentylcarbamoyl, cyclohexylcarbamoyl, etc.], halo(lower)alkanoylcarbamoyl [e.g. trichloroacetylcarbamoyl, etc.], substituted or unsubstituted arylcarbamoyl, for example, arylcarbamoyl [e.g. phenylcarbamoyl, tolylcarbamoyl, xylylcarbamoyl, naphthylcarbamoyl, ethylphenylcarbamoyl, etc.], arylthiocarbamoyl [e.g. phenylthiocarbamoyl, etc.], lower alkoxy-arylcarbamoyl [e.g. methoxyphenylcarbamoyl, etc.], halo-arylcarbamoyl [e.g. fluorophenylcarbamoyl, chlorophenylcarbamoyl, etc.], halo(lower)alkyl-arylcarbamoyl [e.g. trifluoromethylphenylcarbamoyl, etc.], nitro-arylcarbamoyl [e.g. nitrophenylcarbamoyl, etc.], cyano-arylcarbamoyl [e.g. cyanophenylcarbamoyl, etc.], hydroxy(lower)alkyl-arylcarbamoyl [e.g. hydroxymethylphenylcarbamoyl, hydroxyethylphenylcarbamoyl, etc.], amino-arylcarbamoyl [e.g. aminophenylcarbamoyl, etc.], lower alkylamino-arylcarbamoyl [e.g. methylaminophenylcarbamoyl, ethylaminophenylcarbamoyl, dimethylaminophenylcarbamoyl, etc.], lower alkanoylamino-arylcarbamoyl [e.g. acetylaminophenylcarbamoyl, propionylaminophenylcarbamoyl, etc.], N-(lower alkanoyl)-N-(lower alkyl) amino-arylcarbamoyl [e.g. N-acetyl-N-methylaminophenylcarbamoyl, N-propionyl-N-methylaminophenylcarbamoyl, etc.], lower alkoxy(lower) alkanoylamino-arylcarbamoyl [e.g. methoxyacetylaminophenylcarbamoyl, methoxypropionylaminophenylcarbamoyl, etc.], lower alkoxycarbonyl(lower)alkanoylamino-arylcarbamoyl [e.g. ethoxycarbonylacetylaminophenylcarbamoyl, methoxycarbonylpropionylaminophenylcarbamoyl, etc.], carboxyamino-arylcarbamoyl [e.g. carboxyaminophenylcarbamoyl, etc.], lower alkoxycarbonylamino-arylcarbamoyl [e.g. ethoxycarbonylaminophenylcarbamoyl, etc.], aroylamino-arylcarbamoyl [e.g. benzoylaminophenylcarbamoyl, etc.], heterocycliccarbonylamino-arylcarbamoyl [e.g. pyridylcarbonylaminophenylcarbamoyl, furylcarbonylaminophenylcarbamoyl, morpholinocarbonylaminophenylcarbamoyl, etc.], heterocyclic(lower)alkanoylamino-arylcarbamoyl [e.g. pyridylacetylaminophenylcarbamoyl, thienylacetylaminophenylcarbamoyl, etc.], ureidoarylcarbamoyl [e.g. ureidophenylcarbamoyl, etc.], lower alkylureido-arylcarbamoyl [e.g. methylureidophenylcarbamoyl, ethylureidophenylcarbamoyl, etc.], hydroxyimino(lower)alkyl-arylcarbamoyl [e.g. hydroxyiminoethylphenylcarbamoyl, etc.], lower alkoxyimino(lower)alkyl-arylcarbamoyl [e.g. methoxyiminoethylphenylcarbamoyl, etc.], lower alkylhydrazono(lower)alkyl-arylcarbamoyl [e.g. methylhydrazonoethylphenyicarbamoyl, dimethylhydrazonoethylphenylcarbamoyl, etc.], optionally substituted heterocyclic-arylcarbamoyl [e.g. oxopyrrolidinylphenylcarbamoyl, oxopiperidinophenylcarbamoyl, dioxopyrrolidinylphenylcarbamoyl, oxooxazolidinylphenylcarbamoyl, pyrrolylphenylcarbamoyl, etc.], acyl-arylcarbamoyl, for example, carboxy-arylcarbamoyl [e.g. carboxyphenylcarbamoyl, etc.], lower alkoxycarbonyl-arylcarbamoyl [e.g. ethoxycarbonylphenylcarbamoyl, etc.], heterocycliccarbonyl-arylcarbamoyl [e.g. morpholinocarbonylphenylcarbamoyl, pyrrolidinylcarbonylphenylcarbamoyl, piperidinocarbonylphenylcarbamoyl, 1,2,3,6-tetrahydropyridylcarbonylphenylcarbamoyl, piperazinylcarbonylphenylcarbamoyl, thiomorpholinocarbonylphenylcarbamoyl, etc.], heterocycliccarbonyl-arylcarbamoyl substituted with lower alkyl [e.g. methylpiperazinylcarbonylphenylcarbamoyl, ethylpiperazinylcarbonylphenylcarbamoyl, etc.], heterocycliccarbonyl-arylcarbamoyl substituted with aryl [e.g. phenylpiperazinylcarbonylphenylcarbamoyl, etc.], heterocycliccarbonyl-arylcarbamoyl substituted with a heterocyclic group [e.g. pyridylpiperazinylcarbonylphenylcarbamoyl, etc.], heterocycliccarbonyl-arylcarbamoyl substituted with lower alkanoyl [e.g. acetylpiperazinylcarbonylphenylcarbamoyl, etc.], heterocycliccarbonylarylcarbamoyl substituted with lower alkoxycarbonyl [e.g. ethoxycarbonylpiperazinylcarbonylphenylcarbamoyl, etc.], heterocycliccarbonyl-arylcarbamoyl substituted with lower alkylamino [e.g. methylaminopiperazinylcarbonylphenylcarbamoyl, dimethylaminopiperidinocarbonylphenylcarbamoyl, etc.], heterocycliccarbonyl-arylcarbamoyl substituted with lower alkylcarbamoyl [e.g. methylcarbamoylpiperazinylcarbonylphenylcarbamoyl, etc.], carbamoyl-aryicarbamoyl [e.g. carbamoylphenylcarbamoyl, etc.], lower alkylcarbamoyl-arylcarbamoyl [e.g. methylcarbamoylphenylcarbamoyl, ethylcarbamoylphenylcarbamoyl, propylcarbamoylphenylcarbamoyl, dimethylcarbamoylphenylcarbamoyl, diethylcarbamoylphenylcarbamoyl, N-ethyl-N-methylcarbamoylphenylcarbamoyl, N-isopropyl-N-methylcarbamoylphenylcarbamoyl, etc.], hydroxy(lower)alkylcarbamoyl-arylcarbamoyl [e.g. hydroxymethylcarbamoylphenylcarbamoyl, hydroxyethylcarbamoylphenylcarbamoyl, bis(hydroxyethyl)carbamoylphenylcarbamoyl, etc.], N-[hydroxy(lower)alkyl]-N-(lower alkyl)carbamoyl-arylcarbamoyl [e.g. N-(hydroxyethyl)-N-methylcarbamoylphenylcarbamoyl, etc.], lower alkoxy(lower)alkylcarbamoyl-arylcarbamoyl [e.g. methoxymethylcarbamoylphenylcarbamoyl, methoxyethylcarbamoylphenylcarbamoyl, ethoxyethylcarbamoylphenylcarbamoyl, bis(methoxyethyl)carbamoylphenylcarbamoyl, bis(ethoxyethyl)carbamoylphenylcarbamoyl, etc.], N-[lower alkoxy(lower)alkyl]-N-(lower alkyl)carbamoyl-arylcarbamoyl [e.g. N-(methoxyethyl)-N-methylcarbamoylphenylcarbamoyl, N-(methoxypropyl)-N-methylcarbamoylphenylcarbamoyl, etc.], lower alkylamino(lower)alkylcarbamoyl-arylcarbamoyl [e.g. methylaminoethylcarbamoylphenylcarbamoyl, dimethylaminoethylcarbamoylphenylcarbamoyl, etc.], N-[lower alkylamino(lower)alkyl]-N-(lower alkyl)carbamoyl-arylcarbamoyl [e.g. N-(dimethylaminoethyl)-N-methylcarbamoylphenylcarbamoyl, N-(dimethylaminopropyl)-N-methylcarbamoylphenylcarbamoyl, etc.], heterocycliccarbamoyl-arylcarbamoyl [e.g. morpholinylcarbamoylphenylcarbamoyl, thienylcarbamoylphenylcarbamoyl, pyridylcarbamoylphenylcarbamoyl, pyrimidinylcarbamoylphenylcarbamoyl, etc.], N-(heterocyclic)-N-(lower alkyl)carbamoyl-arylcarbamoyl [e.g. N-pyridyl-N-methylcarbamoylphenylcarbamoyl, etc.], heterocyclic(lower)alkylcarbamoyl-arylcarbamoyl [e.g. pyridylmethylcarbamoylphenylcarbamoyl, pyridylethylcarbamoylphenylcarbamoyl, thienylmethylcarbamoylphenylcarbamoyl, etc.], N-[heterocyclic (lower) alkyl]-N-(lower alkyl)carbamoyl-arylcarbamoyl [e.g. N-pyridylmethyl-N-methylcarbamoylphenylcarbamoyl, etc.], N-[heterocyclic(lower)alkyl]-N-[lower alkoxy(lower)alkyl]-carbamoyl-arylcarbamoyl [e.g. N-pyridylmethyl-N-methoxyethylcarbamoylphenylcarbamoyl, etc.], arylcarbamoyl-arylcarbamoyl [e.g. phenylcarbamoylphenylcarbamoyl, etc.], lower alkylamino-arylcarbamoyl-arylcarbamoyl [e.g. dimethylaminophenylcarbamoylphenylcarbamoyl, etc.], lower alkanoyl-arylcarbamoyl [e.g. acetylphenylcarbamoyl, propionylphenylcarbamoyl, etc.], etc., etc., ar(lower)alkylcarbamoyl [e.g. benzylcarbamoyl, phenethylcarbamoyl, etc.], heterocycliccarbamoyl [e.g. furylcarbamoyl, thienylcarbamoyl, pyridylcarbamoyl, quinolylcarbamoyl, isoquinolylcarbamoyl, pyrimidinylcarbamoyl, pyrazolylcarbamoyl, etc.], heterocyclic(lower)alkylcarbamoyl [e.g. pyridylmethylcarbamoyl, pyridylethylcarbamoyl, furylmethylcarbamoyl, thienylmethylcarbamoyl, etc.], arylaminocarbamoyl [e.g. phenylaminocarbamoyl, etc.], aroyl-carbamoyl [e.g. benzoylcarbamoyl, etc.], etc., lower alkylsulfonyl [e.g. mesyl, ethylsulfonyl, propylsulfonyl, isopropylsulfonyl, tert-butylsulfonyl, pentylsulfonyl, etc.], arylsulfonyl [e.g. tosyl, phenylsulfonyl, etc.], ar(lower)alkylsulfonyl [e.g. benzylsulfonyl, phenethylsulfonyl, etc.], ar(lower)alkenylsulfonyl [e.g. styrylsulfonyl, cinnamylsulfonyl, etc.], phthaloyl, substituted or unsubstituted amino acid residue mentioned below, or the like.

Suitable "amino acid residue" may include natural or artificial ones, and such amino acid may be glycine, sarcosine, alanine, β-alanine, valine, norvaline, leucine, isoleucine, norleucine, serine, threonine, cysteine, methionine, phenylalanine, phenylglycine, tryptophan, tyrosine, proline, hydroxyproline, glutamic acid, aspartic acid, glutamine, asparagine, lysine, arginine, histidine, ornithine, or the like, in which more preferable one is glycine, sarcosine, alanine, β-alanine and proline, and the most preferable one is glycine. And said amino acid residue may be substituted with suitable substituent(s) such as the above-mentioned lower alkyl, aryl mentioned below, the above-mentioned acyl, ar(lower)alkyl [e.g. benzyl, phenethyl, trityl, etc.], cycloalkyl [e.g. cyclopropyl, cyclobutyl, cyclopentyl, cyclohexyl, cycloheptyl, cyclooctyl, adamantyl, etc.], a heterocyclic group mentioned below, heterocyclic(lower)alkyl [e.g. pyridylmethyl, pyridylethyl, imidazolylmethyl, furylmethyl, thienylmethyl, morpholinomethyl, piperidinomethyl, etc.], substituted or unsubstituted amidino [e.g. amidino, methylamidino, N-ethyl-N'-cyanoamidino, etc.], or the like.

More preferable "amino acid residue" is a group of the formula:

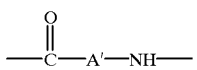

wherein A' is lower alkylene.

Groups of the formula:

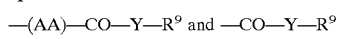

wherein $R_9$, (AA) and Y are each as defined above, are also included within "acyl".

Suitable "aryl" and aryl moiety such as in the term "ar(lower)alkenoyl", etc., may be phenyl, naphthyl, phenyl or naphthyl substituted with lower alkyl [e.g. tolyl, xylyl, mesityl, cumenyl, di(tert-butyl)phenyl, methylnaphthyl, etc.] and the like, in which preferable one is phenyl, naphthyl and tolyl.

Suitable "ar(lower)alkyl" may be benzyl, phenethyl, phenylpropyl, naphthylmethyl, benzhydryl, trityl or the like.

Suitable "heterocyclic group" and heterocyclic moiety such as in the terms "heterocyclic(lower)alkyl", "heterocyclic(lower)alkenyl", "heterocyclic(lower) alkanoyl", "heterocyclic(lower)alkenoyl, etc., may be saturated or unsaturated, monocyclic or polycyclic heterocyclic group containing at least one hetero-atom such as an oxygen, sulfur and/or nitrogen atom such as:

unsaturated 3 to 8-membered, preferably 5 or 6-membered heteromonocyclic group containing 1 to 4 nitrogen atom(s), for example, pyrrolyl, pyrrolinyl, imidazolyl, pyrazolyl, pyridyl, and its N-oxide, pyrimidinyl, pyrazinyl, pyridazinyl, triazolyl, tetrazolyl, dihydrotriazinyl, etc.;

saturated 3 to 8-membered, preferably 4 or 6-membered heteromonocyclic group containing 1 to 4 nitrogen atom(s), for example, azetidinyl, pyrrolidinyl, imidazolidinyl, piperidyl, pyrazolidinyl, piperazinyl, etc.;

unsaturated condensed 7 to 12-membered heterocyclic group containing 1 to 5 nitrogen atom(s), for example, indolyl, isoindolyl, indolizinyl, benzimidazolyl, quinolyl, isoquinolyl, tetrahydroquinolyl, indazolyl, benzotriazolyl, imidazopyridyl, etc.;

unsaturated 3 to 8-membered, preferably 5 or 6-membered heteromonocyclic group containing an oxygen atom, for example, furyl, etc.;

unsaturated condensed 7 to 12-membered heterocyclic group containing 1 to 2 oxygen atom(s), for example, benzofuryl, piperonyl, etc.;

unsaturated 3 to 8-membered, preferably 5 or 6-membered heteromonocyclic group containing a sulfur atom, for example, thienyl, etc.;

unsaturated condensed 7 to 12-membered heterocyclic group containing 1 to 2 sulfur atom(s), for example, benzothienyl, etc.;

unsaturated 3 to 8-membered, preferably 5 or 6-membered heteromonocyclic group containing 1 to 2 oxygen atom(s) and 1 to 3 nitrogen atom(s), for example, oxazolyl, isoxazolyl, oxadiazolyl, etc.;

saturated 3 to 8-membered, preferably 5 or 6-membered heteromonocyclic group containing 1 to 2 oxygen atom(s) and 1 to 3 nitrogen atom(s), for example, morpholinyl, etc.;

unsaturated condensed 7 to 12-membered heterocyclic group containing 1 to 2 oxygen atom(s) and 1 to 3 nitrogen atom(s), for example, benzoxazolyl, benzoxadiazolyl, etc.;

unsaturated 3 to 8-membered, preferably 5 or 6-membered heteromonocyclic group containing 1 to 2 sulfur atom(s) and 1 to 3 nitrogen atom(s), for example, thiazolyl, isothiazolyl, thiazolinyl, thiadiazolyl, etc.;

saturated 3 to 8-membered, preferably 5 or 6-membered heteromonocyclic group containing 1 to 2 sulfur atom(s) and 1 to 3 nitrogen atom(s), for example, thiazolidinyl, etc.;

unsaturated condensed 7 to 12-membered heterocyclic group containing 1 to 2 sulfur atom(s) and 1 to 3 nitrogen atom(s), for example, benzothiazolyl, benzothiadiazolyl, benzothiazinyl, benzothiazolinyl, etc., or the like.

Suitable "lower alkylene" may be a straight or branched one such as methylene, ethylene, trimethylene, methylmethylene, tetramethylene, ethylethylene, propylene, pentamethylene, hexamethylene or the like, in which the most preferable one is methylene.

Suitable "lower alkenylene" may be a straight or branched $C_2$–$C_6$ alkenylene such as vinylene, methylvinylene, propenylene, 1,3-butadienylene or the like, in which the most preferable one is vinylene.

Suitable "a leaving group" may be a conventional acid residue such as halogen [e.g. fluoro, chloro, bromo and iodo], arenesulfonyloxy [e.g. benzenesulfonyloxy, tosyloxy, etc.], alkanesulfonyloxy [e.g. mesyloxy, ethanesulfonyloxy, etc.], and the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid addition salt [e.g. formate, acetate, trifluoroacetate, maleate, tartrate, oxalate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. arginine salt, aspartic acid salt, glutamic acid salt, etc.], an intramolecular salt and the like.

With respect to the salts of the compounds [Ia] and [Ib] in the Process 2, it is to be noted that these compounds are included within the scope of the compound [I], and accordingly the suitable examples of the salts of these compounds are to be referred to those as exemplified for the object compound [I].

Preferred embodiments of the object compound [I] are as follows:

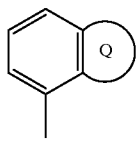 Q is a group of the formula:

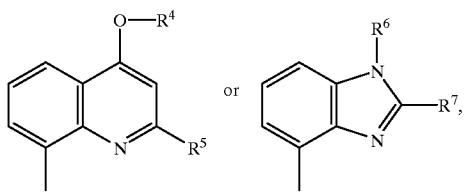

wherein
R⁴ is heterocyclic(lower)alkyl [more preferably, pyridyl (lower)alkyl (most preferably, pyridylmethyl), etc.],
R⁵ is lower alkyl,
R⁶ is acyl(lower)alkyl [more preferably, lower alkoxycarbonyl(lower)alkyl (most preferably, methoxycarbonylmethyl or ethoxycarbonylmethyl), lower alkylcarbamoyl(lower)alkyl (most preferably, methylcarbamoylmethyl or dimethylcarbamoylmethyl), etc.], ar(lower)alkyl [most preferably, benzyl] or heterocyclic(lower)alkyl [more preferably, pyridyl (lower)alkyl (most preferably, pyridylmethyl), etc.], and
R⁷ is lower alkyl or lower alkoxy,
R¹ is hydrogen, lower alkyl or halogen,
R² is lower alkyl or halogen,
R³ is a group of the formula:

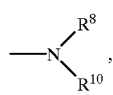

wherein
R⁸ is hydrogen or lower alkyl,
R¹⁰ is acyl [more preferably,
a group of the formula:

—(AA)—CO—Y—R⁹', etc.

in which
R⁹' is phenyl or pyridyl, each of which may be substituted with substituent(s) selected from the group consisting of amino, acyl (more preferably, lower alkoxycarbonyl, lower alkylcarbamoyl, pyridyl(lower)alkylcarbamoyl, pyridylcarbamoyl, etc.), acylamino (more preferably, lower alkanoylamino, pyridylcarbonylamino optionally substituted with lower alkyl, pyridyl(lower) alkanoylamino, etc.), lower alkyl, lower alkoxy, heterocyclic(lower)alkenyl (more preferably, pyridyl(lower)alkenyl, etc.) and a heterocyclic group optionally substituted with oxo (more preferably, oxopyrrolidinyl, etc.),
(AA) is amino acid residue (most preferably, glycyl), and
Y is lower alkenylene (most preferably, vinylene) or NH], or a group of the formula:

—Z—A²—R¹¹, in which
R¹¹ is amino or acylamino,[more preferably, amino, lower alkanoylamino, a group of the formula:

—NH—CO—Y—R⁹', etc.

in which R⁹ and Y are each as defined above],
A² is lower alkylene [most preferably, methylene] or a single bond, and
Z is lower alkenylene or a group of the formula:

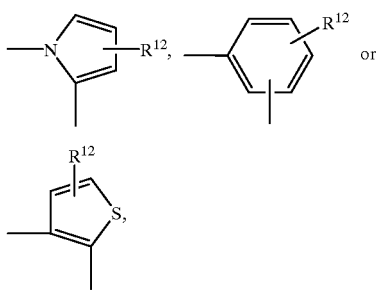

in which
R¹² is hydrogen or halogen, and
A¹ is lower alkylene [most preferably, methylene].

The processes for preparing the object compound [I] are explained in detail in the following.

Process 1

The object compound [I] or its salt can be prepared by reacting a compound [II] or its salt with a compound [III] or its salt.

Suitable salts of the compounds [II] and [III] may be the same as those exemplified for the compound [I].

The reaction is preferably carried out in the presence of a base such as alkali metal [e.g. lithium, sodium, potassium, etc.], the hydroxide or carbonate or bicarbonate thereof [e.g. sodium hydroxide, potassium carbonate, potassium bicarbonate, etc.], alkali metal alkoxide [e.g. sodium methoxide, sodium ethoxide, potassium tert-butoxide, etc.], or the like.

This reaction is usually carried out in a conventional solvent such as tetrahydrofuran, dioxane, N,N-dimethylformamide, acetone, or the like.

The reaction temperature is not critical, and the reaction is usually carried out under cooling to heating.

Process 2

The object compound [Ib] or its salt can be prepared by reacting a compound [Ia] or its salt with a compound [IV] or its reactive derivative at the carboxy group or a salt thereof.

Suitable reactive derivative at the carboxy group of the compound [IV] may include an acid halide, an acid anhydride, an activated amide, an activated ester, and the like. Suitable examples of the reactive derivatives may be an acid chloride; an acid azide; a mixed acid anhydride with an acid such as dialkylphosphoric acid, sulfuric acid, aliphatic carboxylic acid or aromatic carboxylic acid; a symmetrical acid anhydride; an activated amide with imidazole; or an activated ester [e.g. p-nitrophenyl ester, etc.]. These reactive derivatives can optionally be selected from them according to the kind of the compound [IV] to be used.

Suitable salts of the compound [IV] and its reactive derivative can be referred to the ones as exemplified for the compound [I].

The reaction is usually carried out in a conventional solvent, such as methylene chloride, chloroform, pyridine, dioxane, tetrahydrofuran, N,N-dimethylformamide, or the like. In case that the compound [IV] is used in the free acid form or salt form, it is to carry out the reaction in the presence of a conventional condensing agent such as 1-ethyl-3-(3-dimethylaminopropyl)carbodiimide, N,N'-dicyclohexylcarbodiimide or the like.

The reaction temperature is not critical and the reaction can be carried out under cooling, at ambient temperature, or under heating.

This reaction is preferably carried out in the presence of a conventional inorganic base or in the presence of a conventional organic base.

The object compound [I] and the starting compounds can also be prepared by the methods of Examples and Preparations mentioned below or similar manners thereto or conventional manners.

The compounds obtained by the above processes can be isolated and purified by a conventional method such as pulverization, recrystallization, chromatography, reprecipitation or the like.

It is to be noted that the compound [I] and the other compounds may include one or more stereoisomers and geometrical isomers due to asymmetric carbon atoms and double bonds, and all of such isomers and mixture thereof are included within the scope of this invention.

The compound of the formula [I] and its salt can be in the form of a solvate, which is included within the scope of the present invention. The solvate preferably includes a hydrate and an ethanolate.

The object compound [I] and pharmaceutically acceptable salts thereof possess strong activities as bradykinin agonists, and are useful for the treatment and/or the prevention of renal diseases [e.g. renal failure, nephritis, nephropathy, etc.], heart failure, hypertension [e.g. essential hypertension, pulmonary hypertension, etc.], Meniere's disease, peripheral circulatory disorders [e.g. thromboangiitis obliterans (Buerger's disease), arteriosclerosis obliterans, etc.], cerebral circulatory disorders [e.g. cerebral infarction, cerebral thrombosis, cerebral embolism, etc.], climacteric disturbance, retinochoroidal circulatory disorders, myocardial ischemia, myocardial infarction, postmyocardial infarction syndrome, angina pectoris, restenosis after percutaneous transluminal coronary angioplasty (PTCA), hepatitis, liver cirrhosis, pancreatitis, ileus, diabetes or diabetic complications [e.g. diabetic nephropathy, diabetic neuropathy, diabetic retinopathy, etc.], male infertility, glaucoma, or the like, or for the increase of permeability of blood-brain barrier, in human being or animals.

In order to illustrate the usefulness of the object compound [I], the pharmacological test data of some representative compounds of the compound [I] are shown in the following.

(I) $^3$H-Bradykinin receptor binding (i) Test Method:

(a) Crude ileum membrane preparation

Male Hartly strain guinea pigs were sacrificed by decapitation. The ileum was removed and homogenized in buffer (50 mM 2-[[tris(hydroxymethyl)methyl]amino]-1-ethanesulfonic acid (TES), 1 mM 1,10-phenanthroline pH 6.8). The homogenate was centrifuged (1000×g, 20 minutes) to remove tissue clumps and the supernatant was centrifuges (100,000×g, 60 minutes) to yield a pellet. The pellet was resuspended in buffer (50 mM TES, 1 mM 1,10-phenanthroline, 140 mg/l bacitracin, 1 mM dithiothreiol, 0.1% bovine serum albumin pH 6.8) and homogenized with a glass-teflon homogenizer to yield suspension which was referred to as crude membrane suspension. The obtained membrane suspension was stored at −80° C. until use.

(b) $^3$H-Bradykinin binding to the membrane

The frozen crude membrane suspension was thawed. In binding assays, $^3$H-Bradykinin (0.06 nM) and drug were incubated with 50 µl of the membrane suspension at room temperature for 60 minutes in a final volume of 250 µl. Separation of receptor-bound from free $^3$H-Bradykinin is achieved by immediate filtration under vacuum and washed three times with 5 ml of ice-cold buffer (50 mM Tris-HCl pH 7.5). Non-specific binding was defined as binding in the presence of 0.1 µM Bradykinin. The radioactivity retained on rinsed filters was determined by a liquid-scintillation counter.

(ii) Result

| Test Compound (Example No.) | Inhibition of $^3$H-Bradykinin binding: IC$_{50}$ (M) |
|---|---|
| 1-(2) | 9.9 × 10$^{-10}$ |
| 9 | 6.3 × 10$^{-9}$ |

(II) Prostaglandin E2 (PGE2) production in human fibroblasts (i) Test Method:

The assay of PGE2 production was modified from the procedure described in The Journal of Biological Chemistry, 257, 8630–8633 (1982).

(a) Maintenance of cells

Human fibroblasts (WI-38, ATCC CCL75) were grown in Eagle's Minimum Essential Medium [E-MEM: ICN Biomedical Inc., Cat. No. 10-101-24 (47.6 g) with sodium bicarbonate (11.0 g), penicillin G potassium salt (0.5 g), streptomycin sulfate (0.5 g) in water (5000 ml) and 10% fetal bovine serum]. The cells were placed into the quiescent state after confluence was reached.

(b) Measurements of PGE2 production

WI-38 cells were seeded in 24-well plates at a density of 1×10$^5$ cells/well with 0.5 ml of E-MEM including 1% fetal bovine serum and were cultured for 1 day. The mediums in 24-well plates in which WI-38 cells were cultured were removed by aspiration and Hanks-bovine serum albumin buffer [Hanks-BSA Buffer: Hanks' balanced salts (4.9 g), sodium bicarbonate (0.1 g) and bovine serum albumin (protease free) (0.5 g)] was added thereto. After Hanks-BSA Buffer was removed by aspiration, different concentrations of a solution of a test compound in Hanks-BSA Buffer (500 µl), which was prepared by diluting a solution of a test compound in dimethyl sulfoxide with Hanks-BSA Buffer, was added thereto, and cells were incubated for 30 minutes at 37° C. Supernatant was collected, and PGE2 level included therein was measured by PGE2 EIA Kit (Cayman Chemical Co.).

(ii) Result

| Test Compound (Example No.) | WI-38 PGE2 production increase ratio (concentration: 1 × 10$^{-6}$M) |
|---|---|
| 1-(2) | 7.95 |
| 9 | 10.8 |

The compound [I] and a pharmaceutically acceptable salt thereof may also possess activities as bradykinin antagonists at a certain concentration of the compound.

For therapeutic purpose, the compound [I] and a pharmaceutically acceptable salt thereof of the present invention can be used in a form of pharmaceutical preparation containing one of said compounds, as an active-ingredient, in admixture with a pharmaceutically acceptable carrier such as an organic or inorganic solid, semi-solid or liquid excipient suitable for oral, parenteral such as intravenous, intramuscular, subcutaneous or intraarticular, external such as topical, enteral, intrarectal, transvaginal, inhalant, ophthalmic, nasal of hypoglossal administration. The pharmaceutical preparations may be capsules, tablets, dragees, granules, suppositories, solution, lotion, suspension, emulsion, ointment, gel, cream, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for preventing and/or treating the above-mentioned diseases. In general, amounts between 0.1 mg/body and about 1,000 mg/body may be administered per day.

EXAMPLES

The following Preparations and Examples are given for the purpose of illustrating this invention.

Preparation 1

(1) To a mixture of 4-hydroxymethyl-2-methoxybenzoic acid (1.5 g), triethylamine (5 g), dichloromethane (3 ml) and dimethyl sulfoxide (3 ml) was added portionwise sulfur trioxide pyridine complex (3.93 g) in water bath, and the mixture was stirred for 1.5 hours at the same temperature. The reaction mixture was poured into water and extracted with dichloromethane. The organic layer was washed with water and brine, dried over magnesium sulfate and evaporated in vacuo to give 4-formyl-2-methoxybenzoic acid.

NMR (CDCl$_3$, δ): 4.04 (3H, s), 7.47–7.55 (2H, m), 8.04 (1H, d, J=8 Hz), 10.21 (1H, s)

(2) To a suspension of 4-formyl-2-methoxybenzoic acid obtained above in tetrahydrofuran was added methyl (triphenylphosphoranylidene)acetate (3.3 g) at ambient temperature, and the mixture was stirred for 1 hour at the same temperature. The mixture was concentrated in vacuo, and ethyl acetate and saturated sodium bicarbonate solution were added thereto. The separated aqueous layer was adjusted to pH 4 with 1N hydrochloric acid and extracted with ethyl acetate. The extract was washed with water and brine, dried over magnesium sulfate and evaporated in vacuo. The residue was washed with hot diisopropyl ether to give methyl 4-carboxy-3-methoxycinnamate (1.2 g).

NMR (CDCl$_3$, δ): 3.84 (3H, s), 4.13 (3H, s), 6.54 (1H, d, J=16 Hz), 7.14 (1H, s), 7.31 (1H, d, J=8 Hz), 7.67 (1H, d, J=16 Hz), 8.21 (1H, d, J=8 Hz)

(3) To a solution of methyl 4-carboxy-3-methoxycinnamate (400 mg) in N,N-dimethylformamide were added methylamine hydrochloride (126 mg), I-ethyl-3-(3-dimethylaminopropyl)-carbodiimide hydrochloride (390 mg) and 1-hydroxybenzotriazole (320 mg) at ambient temperature, and the mixture was stirred for 18 hours at the same temperature. The reaction mixture was poured into water and extracted with ethyl acetate. The organic layer was washed with water, saturated sodium bicarbonate solution and brine, dried over magnesium sulfate and evaporated in vacuo. The residue was purified by column chromatography on silica gel (chloroform: methanol=40:1, v/v) to give methyl 3-methoxy-4-(methylcarbamoyl)cinnamate (319 mg).

NMR (CDCl$_3$, δ): 3.01 (3H, d, J=5 Hz), 3.82 (3H, s), 4.00 (3H, s), 6.48 (1H, d, J=16 Hz), 7.07 (1H, s), 7.25 (1H, d, J=8 Hz), 7.67 (1H, d, J=16 Hz), 7.78 (1H, br s), 8.24 (1H, d, J=8 Hz)

(4) To a solution of methyl 3-methoxy-4-(methylcarbamoyl)-cinnamate (300 mg) in methanol was added 1H aqueous sodium hydroxide solution (1.5 ml) at ambient temperature, and the mixture was stirred for 5 hours at 50° C. The solvent was removed, and water was added thereto. The mixture was washed with diethyl ether and adjusted to pH 4 with 1N hydrochloric acid. The resulting precipitate was collected by filtration and washed with water to give 3-methoxy-4-(methylcarbamoyl)-cinnamic acid (250 mg).

NMR (DMSO-d$_6$, δ): 2.78 (3H, d, J=5 Hz), 3.91 (3H, s), 6.66 (1H, d, J=16 Hz), 7.31 (1H, d, J=8 Hz), 7.43 (1H, s), 7.59 (1H, d, J=16 Hz), 7.73 (1H, d, J=8 Hz), 8.16 (1H, q-like)

Preparation 2

(1) To a suspension of lithium aluminum hydride (31.1 mg) in tetrahydrofuran (1 ml) was dropwise added a solution of methyl 2-[(E)-2-(4-pyridyl)vinyl]pyridine-5-carboxylate (385 mg) in tetrahydrofuran (10 ml) at 0° C. under nitrogen atmosphere, and the mixture was stirred for 45 minutes at the same temperature. Aqueous ammonia was dropwise added thereto at 0° C. and then methanol (5 ml) was further added thereto, and the mixture was stirred for 2 hours. After filtration the filtrate was concentrated in vacuo. The residue was dissolved in dichloromethane, and the solution was washed with water and brine and dried over magnesium sulfate. The solvent was removed in vacuo, and the residue was washed with diisopropyl ether to give 5-hydroxymethyl-2-[(E)-2-(4-pyridyl)vinyl]pyridine (251 mg).

mp:>198.9° C. NMR (CDCl$_3$, δ): 4.73 (2H, s), 7.34 (1H, d, J=16 Hz), 7.40–7.49 (3H, m), 7.53 (1H, d, J=16 Hz), 8.53–8.65 (3H, m)

(2) 5-Formyl-2-[(E)-2-(4-pyridyl)vinyl]pyridine was obtained according to a similar manner to that of Preparation 1-(1).

mp: 131–136° C. NMR (CDCl$_3$, δ): 7.40 (1H, d, J=16 Hz), 7.47 (2H, d, J=6 Hz), 7.56 (1H, d, J=8 Hz), 7.78 (1H, d, J=16 Hz), 8.19 (1H, dd, J=2, 8 Hz), 8.65 (2H, d, J=6 Hz), 9.07 (1H, d, J=2 Hz), 10.12 (1H, s)

(3) Methyl (E)-3-[6-[(E)-2-(4-pyridyl)vinyl]pyridin-3-yl]acrylate was obtained according to a similar manner to that of Preparation 1-(2).

mp:>143.2° C. NMR (CDCl$_3$, δ): 3.83 (3H, s), 6.53 (1H, d, J=16 Hz), 7.34 (1H, d, J=16 Hz), 7.40–7.47 (3H, m), 7.64 (1H, d, J=16 Hz), 7.70 (1H, d, J=16 Hz), 7.87 (1H, d, J=8 Hz), 8.63 (2H, d, J=6 Hz), 8.75 (1H, d, J=2 Hz)

(4) (E)-3-[6-[(E)-2-(4-Pyridyl)vinyl]pyridin-3-yl]acrylic acid was obtained according to a similar manner to that of Preparation 1-(4).

mp:>250° C. NMR (DMSO-d$_6$, δ): 6.71 (1H, d, J=16 Hz), 7.56–7.77 (6H, m), 8.20 (1H, dd, J=2, 8 Hz), 8.59 (2H, d, J=6 Hz), 8.88 (1H, d, J=2 Hz)

Preparation 3

(1) 3-(N-Glycyl-N-methylamino)-1-(tert-butyldiphenyl-silyloxymethyl)-2,6-dichlorobenzene was obtained from 1-(tert-butyldiphenylsilyloxymethyl)-2,6-dichloro-3-[N-methyl-N-(phthalimidoacetyl)amino]benzene according to a similar manner to that of Example 3-(2).

NMR (CDCl$_3$, δ): 1.05 (9H, s), 2.94 (1H, d, J=17 Hz), 3.09 (1H, d, J=17 Hz), 3.20 (3H, s), 4.93 (2H, s), 7.18 (1H, d, J=8 Hz), 7.35–7.49 (7H, m), 7.69–7.77 (4H, m)

(2) 1-(tert-Butyldiphenylsilyloxymethyl)-2,6-dichloro-3-[N-methyl-N-[4-(methylcarbamoyl)cinnamoylglycyl]amino]benzene was obtained by reacting 3-(N-glycyl-N-methylamino)-1-(tert-butyldiphenylsilyloxymethyl)-2,6-dichlorobenzene with 4-(methylcarbamoyl)cinnamic acid according to a similar manner to that of Example 3-(3).

mp: 219–222° C. NMR (CDCl$_3$, δ): 1.05 (9H, s), 3.02 (3H, d, J=5 Hz), 3.21 (3H, s), 3.56 (1H, dd, J=17.4 Hz), 3.93 (1H, dd, J=17, 5 Hz), 4.91 (1H, d, J=10 Hz), 4.98 (1H, d, J=10 Hz), 6.15 (1H, br d, J=5 Hz), 6.51 (1H, d, J=15 Hz), 6.63 (1H, br s), 7.19–7.28 (2H, m), 7.32–7.48 (6H, m), 7.50–7.60 (3H, m), 7.68–7.78 (6H, m)

(3) To a suspension of 1-(tert-butyldiphenylsilyloxymethyl)-2,6-dichloro-3-[N-methyl-N-[4-(methylcarbamoyl)-cinnamoylglycyl]amino]benzene (17.6 g) in tetrahydrofuran (138 ml) was added 1M tetrabutylammonium fluoride in tetrahydrofuran (38.4 ml) at ambient temperature. The reaction mixture was stirred for 1 hour. The mixture was concentrated and diluted with dichloromethane. The organic layer was washed with 1H hydrochloric acid, saturated sodium bicarbonate solution and water, dried over magnesium sulfate and evaporated in vacuo to give 2,6-dichloro-1-hydroxymethyl-3-[N-methyl-N-[4-(methylcarbamoyl)cinnamoylglycyl]amino]-benzene (8.14 g).

mp: 207–211° C. NMR (DMSO-d$_6$, δ): 2.79 (3H, d, J=5 Hz), 3.11 (3H, s), 3.47 (1H, dd, J=17, 4 Hz), 3.77 (1H, dd, J=17, 5 Hz), 4.74 (1H, d, J=5 Hz), 5.34 (1H, t, J=5 Hz), 6.87 (1H, d, J=15 Hz), 7.40 (1H, d, J=15 Hz), 7.59–7.68 (4H, m), 7.85 (2H, d, J=8 Hz), 8.29 (1H, t, J=5 Hz), 8.48 (1H, d, J=5 Hz)

(4) To a mixture of 2,6-dichloro-1-hydroxymethyl-3-[N-methyl-N-[4-(methylcarbamoyl)cinnamoylglycyl]amino]benzene (8.10 g) in dichloromethane (81 ml) was added triphenylphosphine (5.66 g) and carbon tetrabromide (8.95 g) at 0° C. After 15 minutes the reaction mixture was stirred at ambient temperature for 3 hours. To the mixture was added triphenylphosphine (1.42 g) and carbon tetrabromide (2.39 g) and stirred for another 2 hours. The reaction mixture was washed with saturated sodium hydrogen carbonate, water and brine. After dried over anhydrous magnesium sulfate, the mixture was filtered and evaporated in vacuo. The residue was purified by flash column chromatography eluting with dichloromethane:ethyl acetate (1:1, V/V) and dichloromethane:methanol (20:1, V/V) followed by crystallizing from ethyl acetate to give 2,6-dichloro-3-[N-methyl-N-[4-(methylcarbamoyl)cinnamoylglycyl]amino]benzyl bromide (6.40 g) as pale yellow crystals.

mp: 211.6–216.5° C. NMR (CDCl$_3$, δ): 3.02 (3H, d, J=5 Hz), 3.27 (3H, s), 3.62 (1H, dd, J=17, 4 Hz), 3.92 (1H, dd, J=17, 5 Hz), 4.78 (1.2H, s), 4.90 (0.8H, s), 6.15 (1H, br d, J=5 Hz), 6.51 (1H, d, J=15 Hz), 6.67 (1H, br t, J=5 Hz), 7.29 (1H, overlapped with H$_2$O), 7.45–7.62 (4H, m), 7.76 (2H, d, J=8 Hz)

Preparation 4

(1) 3-[N-[(E)-3-(6-Acetamidopyridin-3-yl) acryloylglycyl)-N-methylamino]-1-[tert-butyldiphenylsilyloxymethyl]-2,6-dichlorobenzene was obtained by reacting 3-(N-glycyl-N-methylamino)-1-(tert-butyldiphenylsilyloxymethyl)-2,6-dichiorobenzene with (E)-3-(6-acetamidopyridin-3-yl)acrylic acid according to a similar manner to that of Example 3-(3).

mp: 194–196° C. NMR (CDCl$_3$, δ): 1.06 (9H, s), 2.22 (3H, s), 3.23 (3H, s), 3.57 (1H, dd, J=17, 4 Hz), 3.94 (1H, dd, J=17, 5 Hz), 4.92 (1H, d, J=10 Hz), 4.98 (1H, d, J=10 Hz), 6.44 (1H, d, J=15 Hz), 6.63 (1H, br s), 7.22 (1H, d, J=8 Hz), 7.35–7.48 (6H, m), 7.52 (1H, d, J=15 Hz), 7.70–7.77 (4H, m), 7.83 (1H, dd, J=8, 3 Hz), 8.05 (1H, br s), 8.22 (1H, d, J=8 Hz), 8.36 (1H, d, J=3 Hz)

(2) 3-[N-(E)-3-(6-Acetamidopyridin-3-yl) acryloylglycyl]-N-methylamino]-1-hydroxymethyl-2,6-dichlorobenzene was obtained according to a similar manner to that of Preparation 3-(3).

mp: 207–209° C. NMR (DMSO-d$_6$, δ): 2.10 (3H, s), 3.10 (3H, s), 3.47 (1H, dd, J=17, 4 Hz), 3.76 (1H, dd, J=17, 5 Hz), 4.74 (1H, d, J=5 Hz), 5.35 (1H, br s), 6.79 (1H, d, J=15 Hz), 7.37 (1H, d, J=15 Hz), 7.61 (1H, d, J=8 Hz), 7.65 (1H, d, J=8 Hz), 7.98 (1H, dd, J=8, 3 Hz), 8.11 (1H, d, J=8 Hz), 8.21 (1H, t, J=5 Hz), 8.47 (1H, s)

(3) 3-[N-[(E)-3-(6-Acetamidopyridin-3-yl) acryloylglycyl]-N-methylamino]-1-hydroxymethyl-2,6-dichlorobenzene (5.36 g) was dissolved in N,N-dimethylformamide (30 ml) under nitrogen atmosphere, triethylamine (2.4 g) and methanesulfonyl chloride (1.3 ml) were added to the mixture at 0° C., and the mixture was stirred at 0° C. for 1 hour and at ambient temperature for 18 hours. The reaction mixture was poured into water and extracted with chloroform. The organic layer was separated, washed with saturated aqueous solution of sodium hydrogen carbonate and brine, dried over magnesium sulfate and evaporated in vacuo. The residue was washed with ethyl acetate to give 3-[N-[(E)-3-(6-acetamidopyridin-3-yl) acryloylglycyl]-N-methylamino]-2,6-dichlorobenzyl chloride (5–1 g) as a powder.

NMR (DMSO-d$_6$, δ): 2.10 (3H, s), 3.10 (3H, s), 3.45 (1H, dd, J=4, 16 Hz), 3.74 (1H, dd, J=4, 16 Hz), 4.97 (2H, s), 6.77 (1H, d, J=16 Hz), 7.35 (1H, d, J=16 Hz), 7.73 (1H, s-like), 7.98 (1H, d, J=8 Hz), 8.11 (1H, d, J=8 Hz), 8.24 (1H, t-like), 8.45 (1H, d, J=2 Hz)

Preparation 5

(1) 3-(3-[N-[(E)-3-(6-Acetamidopyridin-3-yl) acryloylglycyl]-N-methylamino]-2,6-dichlorobenzyloxy]-2-aminoaniline was obtained by reacting 3-hydroxy-2-aminoaniline with 3-[N-[(E)-3-(6-acetamidopyridin-3-3-yl)acryloylglycyl]-N-methylamino]-2,6-dichlorobenzyl chloride according to a similar manner to that of Example 1-(2).

NMR (CDCl$_3$, δ): 2.22 (3H, s), 3.28 (3H, s), 3.50 (4H, br s), 3.69 (1H, dd, J=17, 4 Hz), 3.94 (1H, dd, J=17, 5 Hz), 5.34 (2H, s), 6.40–6.50 (2H, m), 6.60–6.76 (3H, m), 7.32 (1H, d, J=7.5 Hz), 7.50 (1H, d, J=7.5 Hz), 7.53 (1H, d, J=15 Hz), 7.85 (1H, dd, J=7.5, 2 Hz), 7.27–7.36 (4H, m), 7.49 (1H, d, J=7.5 Hz), 7.51 (1H, d, J=15 Hz), 7.84 (1H, br d, J=7.5 Hz), 8.09 (1H, br s), 8.22 (1H, br d, J=7.5 Hz), 8.36 (1H, br s)

(2) To a solution of 3-[3-[N-[(E)-3-(6-acetamidopyridin-3-yl)acryloylglycyl]-N-methylamino]-2,6-dichlorobenzyloxy]-2-aminoaniline (735 mg) in acetic acid (7.4 ml) was added tetramethyl orthocarbonate (215 mg) at ambient temperature, and the mixture was stirred for 8 hours at the same temperature. The solvent was removed, and the residue was dissolved in chloroform. The solution was washed with saturated sodium bicarbonate solution, water and brine, dried over magnesium sulfate and concentrated in vacuo. The residue was purified by flash chromatography (chloroform-methanol) to give 4-[3-[N-[(E)-3-(6-acetamidopyridin-3-yl)acryloylglycyl]-N-methylamino]-2,6-dichlorobenzyloxy]-2-methoxy-1H-benzimidazole (654 mg).

NMR (CDCl$_3$, δ): 2.21 (3H, s), 3.29 (3H, s), 3.59 (1H, br d, J=17 Hz), 4.10–4.22 (4H, m), 5.30 (1H, d, J=10 Hz), 5.59 (1H, d, J=10 Hz) 6.48 (1H, d, J=15 Hz), 6.78 (1H, br s), 7.83 (1H, d, J=7.5 Hz), 7.12 (1H, t, J=15 Hz), 7.20–7.29 (1H, m), 7.32 (1H, d, J=7.5 Hz), 7.49 (1H, d, J=7.5 Hz), 7.65 (1H, d, J=15 Hz), 7.85 (1H, br d, J=7.5 Hz), 8.09 (1H, br s), 8.23 (1H, br d, J=7.5 Hz), 8.37 (1H, br s)

Preparation 6

(1) A mixture of 2,6-dimethylbenzyl alcohol (17.1 g) and acetic anhydride (14.2 ml) was stirred at 70° C. for 5 hours during which time to the mixture was added 4-dimethylaminopyridine (17 mg). After cooling, the reaction mixture was evaporated in vacuo. The residue was dissolved in ethyl acetate, and the solution was washed with water twice. The organic layer was dried over magnesium sulfate and evaporated in vacuo to give 2,6-dimethylbenzyl acetate (22.50 g) as colorless oil.

NMR (CDCl$_3$, δ): 2.07 (3H, s), 2.38 (6H, s), 5.19 (2H, s), 7.05 (2H, d, J=8 Hz), 7.15 (1H, t, J=8 Hz)

(2) To a solution of acetic anhydride (70 ml) and acetic acid (35 ml) was added copper (II) nitrate trihydrate (34.2 g) in an ice-water bath. To this stirred mixture was added dropwise a solution of 2,6-dimethylbenzyl acetate (21.0 g) in acetic anhydride (21 ml) and acetic acid (10 ml) over 30 minutes. The reaction mixture was stirred for 30 minutes in an ice-water bath and for 30 minutes at ambient temperature. The mixture was poured into ice, extracted with ethyl acetate twice. The organic layer was washed with water three times and brine, dried over magnesium sulfate. The solvent was evaporated in vacuo to give 2,6-dimethyl-3-nitrobenzyl acetate (26.9 g) as pale yellow oil.

NMR (CDCl$_3$, δ): 2.08 (3H, s), 2.47 (3H, s), 2.50 (3H, s), 5.22 (2H, s), 7.18 (1H, d, J=8 Hz), 7.69 (1H, d, J=8 Hz)

(3) To a solution of 2,6-dimethyl-3-nitrobenzyl acetate (26.9 g) in methanol (266 ml) was added aqueous 1N sodium hydroxide solution (133 ml) at ambient temperature for 30 minutes. To the mixture was added water, and the precipitate was collected by filtration to give 2,6-dimethyl-3-nitrobenzyl alcohol (18.0 g) as pale yellow crystals.

mp: 99–102° C. NMR (CDCl$_3$, δ): 1.44 (1H, t, J=5 Hz), 2.50 (3H, s), 2.56 (3H, s), 4.82 (2H, d, J=5 Hz), 7.17 (1H, d, J=8 Hz), 7.66 (1H, d, J=8 Hz)

(4) To a solution of tert-butyldiphenylsilyl chloride (30.7 g) in N,N-dimethylformamide (90 ml) were added 2,6-dimethyl-3-nitrobenzyl alcohol (18.4 g) and imidazole (8.99 g) under ice-cooling, and the mixture was stirred for 15 minutes at the same temperature and for 3 hours at ambient temperature. Water was added thereto, and the mixture was extracted with ethyl acetate. The extract was washed with water and brine, dried over magnesium sulfate and evaporated in vacuo to give 1-(tert-butyldiphenylsilyloxymethyl)-2,6-dimethyl-3-nitrobenzene (46.67 g) as pale yellow oil.

NMR (CDCl$_3$, δ): 1.03 (9H, s), 2.20 (3H, s), 2.38 (3H, s), 5.73 (2H, s), 7.06 (1H, d, J=8 Hz), 7.33-7.49 (6H, m), 7.58–7.73 (5H, m)

(5) To a suspension of 1-(tert-butyldiphenylsilyloxymethyl)-2,6-dimethyl-3-nitrobenzene (42 g) and ammonium chloride (4.2 g) in ethanol (378 ml)-water (42 ml) was added iron (7.0 g), and the mixture was refluxed for 6 hours, during which iron (7.0 g) was added thereto twice. Insoluble materials were filtered off, and the filtrate was concentrated. To the residue was added water and extracted with ethyl acetate. The organic layer was washed with water and brine, dried over magnesium sulfate and concentrated to give 3-amino-1-(tert-butyldiphenylsilyloxymethyl)-2,6-dimethylbenzene (42.8 g) as pale yellow oil.

NMR (CDCl$_3$, δ): 1.04 (9H, s), 2.09 (3H, s), 2.11 (3H, s), 3.48 (2H, br s), 4.70 (2H, s), 6.58 (1H, d, J=8 Hz), 6.71 (1H, d, J=8 Hz), 7.33–7.48 (6H, m), 7.66–7.73 (4H, m)

(6) To a suspension of 3-amino-1-(tert-butyldiphenylsilyloxymethyl)-2,6-dimethylbenzene (42.4 g) in pyridine (17.2 g) and N,N-dimethylformamide (212 ml) was added phthalimidoacetyl chloride (25.6 g) over the period of 15 minutes under ice-cooling, and the mixture was stirred for 1 hour at the same temperature. Water was added thereto, and the resulting precipitate was collected by filtration and washed with acetone to give 1-(tert-butyldiphenylsilyloxymethyl)-2,6-dimethyl-3-(phthalimidoacetylamino)benzene (59.1 g) as colorless crystals.

mp: 207–210° C. NMR (CDCl$_{31}$ δ): 1.02 (9H, s), 2.12 (3H, s), 2.19 (3H, s), 4.52 (2H, s), 4.70 (2H, s), 6.95 (1H, d, J=8 Hz), 7.25–7.50 (7H, m), 7.63–7.80 (6H, m), 7.86–7.96 (2H, m)

(7) To a suspension of 1-(tert-butyldiphenylsilyloxymethyl)-2,6-dimethyl-3-(phthalimidoacetylamino)benzene (57.4 g) and sodium hydride (4.78 g) in N,N-dimethylformamide (287 ml) was dropwise added methyl iodide (15.5 g) under ice-cooling, and the mixture was stirred for 15 minutes at the same temperature and for 2 hours at ambient temperature. Water and ethyl acetate were added thereto, and the resulting precipitate was collected by filtration and washed with water and ethyl acetate to give 1-(tert-butyldiphenylsilyloxymethyl)-2,6-dimethyl-3-[N-methyl-N-(phthalimidoacetyl)amino]benzene (28.18 g) as colorless crystals.

mp: 180–182° C. NMR (CDCl$_3$, δ): 1.04 (9H, s), 2.21 (3H, s), 2.27 (3H, s), 3.17 (3H, s), 3.82 (1H, d, J=17 Hz), 4.12 (1H, d, J=17 Hz), 4.78 (2H, s), 7.09 (1H, d, J=8 Hz), 7.15 (1H, d, J=8 Hz), 7.34–7.49 (6H, m), 7.65–7.73 (6H, m), 7.80–7.88 (2H, m)

(8) 3-(N-Glycyl-N-methylamino)-1-(tert-butyldiphenylsilyloxymethyl)-2,6-dimethylbenzene was obtained according to a similar manner to that of Example 3-(2).

NMR (CDCl$_3$, δ): 1.03 (9H, s), 2.02 (3H, s), 2.22 (3H, s), 2.82 (1H, d, J=17 Hz), 3.09 (1H, d, J=17 Hz), 3.15 (3H, s), 4.72 (2H, s), 6.92 (1H, d, J=8 Hz), 7.01 (1H, d, J=8 Hz), 7.32–7.49 (6H, m), 7.62–7.70 (4H, m)

(9) 1-(tert-Butyldiphenylsilyloxymethyl)-2,6-dimethyl-3-[N-methyl-N-[4-(methylcarbamoyl)cinnamoylglycyl] amino]benzene was obtained according to a similar manner to that of Example 3-(3).

mp: 204–208° C. NMR (CDCl$_3$, δ): 1.05 (9H, s), 2.05 (3H, s), 2.26 (3H, s), 3.02 (3H, d, J=5 Hz), 3.20 (3H, s), 3.52 (1H, dd, J=17, 5 Hz), 3.87 (1H, dd, J=17, 5 Hz), 4.73 (2H, s), 6.16 (1H, br d, J=5 Hz), 6.51 (1H, d, J=15 Hz), 6.69 (1H, br t, J=5 Hz), 6.98 (1H, d, J=8 Hz), 7.06 (1H, d, J=8 Hz), 7.35–7.48 (6H, m), 7.51–7.60 (3H, m), 7.65–7.80 (6H, m)

(10) 2,6-Dimethyl-1-hydroxymethyl-3-[N-methyl-N-[4-(methylcarbamoyl)cinnamoylglycyl]amino]benzene was obtained according to a similar manner to that of Example 3-(3).

mp: 261–263° C. NMR (DMSO-d$_6$, δ): 2.27 (3H, s), 2.40 (3H, s), 2.79 (3H, d, J=5 Hz), 3.08 (3H, s), 3.43 (1H, dd, J=17, 5 Hz), 3.65 (1H, dd, J=17, 5 Hz), 4.53 (2H, d, J=5 Hz), 4.88 (1H, t, J=5 Hz), 6.89 (1H, d, J=15 Hz), 7.15 (2H, s), 7.41 (1H, d, J=15 Hz), 7.64 (2H, d, J=8 Hz), 7.85 (2H, d, J=8 Hz), 8.21 (1H, br t, J=5 Hz), 8.48 (1H, br d, J=8 Hz)

(11) To a solution of 2,6-dimethyl-1-hydroxymethyl-3-[N-methyl-N-[4-(methylcarbamoyl)cinnamoylglycyl] amino]benzene (2.00 g) in N,N-dimethylformamide (100 ml) was added mezhanesulfonyl chloride (784 mg) under ice-cooling, and the mixture was stirred for 2 hours at the same temperature and overnight at ambient temperature. To the mixture was added water and extracted with chloroform. The organic layer was washed with brine, dried over magnesium sulfate and concentrated. The residue was pulverized with diethyl ether to give 2,6-dimethyl-3-[N-[4-(methylcarbamoyl)-cinnamoylglycyl]-N-methylamino]benzyl chloride (2.00 g) as white powder.

mp: 232° C. NMR (CDCl$_3$, δ): 2.29 (3H, s), 2.46 (3H, s), 3.03 (3H, d, J=5 Hz), 3.24 (3H, s), 3.59 (1H, d, J=17, 5 Hz), 3.82 (1H, dd, J=17, 4 Hz), 4.67 (2H, s), 6.20 (1H, m), 6.50 (1H, d, J=15 Hz), 6.70 (1H, d, J=5 Hz), 7.04 (1H, d, J=9 Hz), 7.14 (1H, d, J=9 Hz), 7.50–7.60 (3H, m), 7.75 (2H, d, J=9 Hz)

Example 1

(1) To an ice-cooled solution of 2-hydroxymethylpyridine (164 mg) in anhydrous dimethylimidazolinone (2 ml) was added sodium hydride (40% in oil, 100 mg), and the mixture was stirred at the same temperature for 30 minutes. To this mixture were added 4-chloro-8-hydroxy-2-methylquinoline (194 mg) and tetrabutylammonium iodide (185 mg). The mixture was stirred at 100° C. for 8 hours and partitioned between ethyl acetate and water. The organic layer was separated and the aqueous layer was extracted with ethyl acetate. The organic layers were combined, washed with water three times, dried over magnesium sulfate and evaporated in vacuo. The residue was purified by a silica gel column chromatography (n-hexane–ethyl acetate) followed by trituration with n-hexane to give 8-hydroxy-2-methyl-4-(2-pyridylmethoxy)quinoline (131 mg) as a pale yellow powder.

NMR (CDCl$_3$, δ): 2.64 (3H, s), 5.42 (2H, s), 6.70 (1H, s), 7.15 (1H, d, J=8 Hz), 7.28 (1H, dd, J=6, 5 Hz), 7.37 (1H, t, J=8 Hz), 7.59 (1H, d, J=8 Hz), 7.70 (1H, d, J=8 Hz), 7.75 (1H, dd, J=8, 6 Hz), 8.65 (1H, d, J=5 Hz)

(2) To an ice-cooled mixture of sodium hydride (40% in oil, 9 mg) and anhydrous N,N-dimethylformamide (1 ml) was added 8-hydroxy-2-methyl-4-(2-pyridylmethoxy)quinoline (53 mg), and the mixture was stirred at the same temperature for 30 minutes. To this mixture was added 2,6-dichloro-3-[N-[4-(methylcarbamoyl)cinnamoylglycyl]-N-methylamino]benzyl bromide (103 mg), and the mixture was stirred at ambient temperature for 2.5 hours. Water (2 ml) was slowly added to the reaction mixture under ice-water cooling and the precipitates were collected by vacuum filtration and washed with water and diethyl ether. The crude product was purified by a preparative thin layer chromatography (chloroform-methanol-ammonium hydroxide) followed by trituration with ethyl acetate to give 8-[2,6-dichloro-3-[N-[4-(methylcarbamoyl)cinnamoylglycyl]-N-methylamino]benzyloxy]-2-methyl-4-(2-pyridylmethoxy) quinoline (77 mg) as a pinkish powder.

NMR (CDCl$_3$, δ): 2.63 (3H, s), 3.00 (3H, d, J=6 Hz), 3.25 (3H, s), 3.62 (1H, dd, J=18, 3 Hz), 3.92 (1H, dd, J=18, 4 Hz), 5.40 (2H, s), 5.63 (2H, s), 6.33 (1H, br s), 6.53 (1H, d, J=16 Hz), 6.68–6.78 (2H), 7.22–7.80 (12H), 7.95 (1H, d, J=8 Hz), 8.64 (1H, d, J=5 Hz)

Example 2

8-[3-[N-[(E)-3-(6-Acetamidopyridin-3-yl) acryloylglycyl]-N-methylamino]-2,6-dichlorobenzyloxy]-2-methyl-4-(2-pyridylmethoxy)quinoline was obtained by reacting 8-hydroxy-2-methyl-4-(2-pyridylmethoxy) quinoline with 3-[N-[(E)-3-(6-acetamidopyridin-3-yl) acryloylglycyl]-N-methylamino]-2,6-dichlorobenzyl chloride according to a similar manner to that of Example 1-(2).

NMR (CDCl$_3$, δ) 2.20 (3H, s), 2.65 (3H, s), 3.26 (3H, s), 3.64 (1H, dd, J=4, 18 Hz), 3.94 (1H, dd, J=4, 18 Hz), 5.41 (2H, s), 5.63 (2H, s), 6.46 (1H, d, J=16 Hz), 6.72 (2H, s), 7.21–7.31 (3H, m), 7.41 (1H, t, J=8 Hz), 7.45–7.63 (3H, m), 7.95 (1H, d, J=8 Hz), 8.03 (1H, s-like), 8.19 (1H, d, J=8 Hz), 8.34 (1H, d, J=2 Hz), 8.64 (1H, d, J=6 Hz)

Example 3

(1) To a suspension of sodium hydride (59.5 mg) in N,N-dimethylformamide (0.5 ml) was added a solution of 8-hydroxy-2-methyl-4-(2-pyridylmethoxy)quinoline (600 mg) in N,N-dimethylformamide (5 ml) in ice water bath under nitrogen atmosphere, and the mixture was stirred for 30 minutes at the same condition. To the mixture was dropwise added a solution of 2,6-dichloro-3-[N-methyl-N-(phthalimidoacetyl)amino]benzyl methanesulfonate (1 g) in N,N-dimethylformamide (25 ml) in ice water bath under nitrogen atmosphere, and the mixture was stirred for 2 hours at the same temperature and for 1 day at ambient temperature. The reaction mixture was poured into water and extracted with chloroform. The organic layer was washed with water, saturated sodium bicarbonate solution and brine, dried over magnesium sulfate and evaporated in vacuo. The residue was purified by column chromatography on silica gel (chloroform—methanol) to give 8-[2,6-dichloro-3-[N-methyl-N-(phthalimidoacetyl)amino]benzyloxy]-2-methyl-4-(2-pyridylmethoxy)quinoline (772 mg) as amorphous powder.

NMR (CDCl$_3$, δ): 2.67 (3H, s), 3.21 (3H, s), 4.01 (2H, s), 5.38 (3H, s), 5.67 (1H, d, J=10 Hz), 5.73 (1H, d, J=10 Hz), 6.70 (1H, s), 7.21–7.32 (2H, m), 7.37 (1H, t, J=8 Hz), 7.45 (1H, d, J=8 Hz), 7.52 (1H, d, J=8 Hz), 7.57 (1H, d, J=8 Hz), 7.64–7.80 (3H, m), 7.80–7.89 (2H, m), 7.95 (1H, d, J=8 Hz), 8.64 (1H, d, J=6 Hz)

(2) A mixture of 8-[2,6-dichloro-3-[N-methyl-N-(phthalimidoacetyl)amino]benzyloxy]-2-methyl-4-(2-pyridylmethoxy)quinoline (750 mg), hydrazine monohydrate (117 mg) and ethanol was heated under reflux for 4 hours. The precipitate was removed by filtration and filtrate was evaporated in vacua. The residue was dissolved with a mixture of chloroform and methanol (10:1, V/V), precipitate was removed by filtration and filtrate was evaporated in vacua. The residue was purified by column chromatography on silica gel eluting with chloroform—methanol to afford 8-[3-(N-glycyl-N-methylamino)-2,6-dichlorobenzyloxy]-2-methyl-4-(2-pyridylmethoxy)quinoline (390 mg) as an amorphous powder.

NMR (DMSO-d$_6$, δ): 2.55 (3H, s), 2,76 (1H, d, J=18 Hz), 3.01 (1H, d, J=18 Hz), 3.11 (3H, s), 3.40–3.60 (1H, m), 4.10 (1H, br peak), 5.37–5.63 (4H, m), 7.07 (1H, s), 7.33–7.53 (3H, m), 7.62–7.94 (5H, m), 8.62 (1H, d, J=6 Hz)

(3) To a solution of 8-[3-(N-glycyl-N-methylamino)-2,6-dichlorobenzyloxy]-2-methyl-4-(2-pyridylmethoxy) quinoline (30 mg) and 4-(isonicotinamido)cinnamic acid (17 mg) in N,N-dimethylformamide (2 ml) were added 1-ethyl-3-(3-dimethylaminopropyl)carbodiimide hydrochloride (14 mg) and 1-hydroxybenzotriazole (11 mg) at ambient temperature, and the mixture was allowed to stand for 1 day at ambient temperature. The reaction mixture was poured into water and extracted with chloroform. The organic layer was washed with water and aqueous sodium hydrogen carbonate solution, dried over magnesium sulfate and evaporated in vacua. The residue was purified by preparative thin layer chromatography (chloroform:methanol=10:1, V/V) to give 8-[2,6-dichloro-3-[N-methyl-N-[4-(isonicotinamido)cinnamoylglycyl]amino]-benzyloxy]-2-methyl-4-(2-pyridylmethoxy)quinoline (19 mg) as an amorphous powder.

NMR (CDCl$_3$, δ): 2.56 (3H, s), 3.20 (3H, s), 3.60 (1H, dd, J=4, 18 Hz), 3.86 (1H, dd, J=4, 18 Hz), 5.41 (2H, s), 5.59 (2H, s), 6.42 (1H, d, J=16 Hz), 6.60–6.76 (2H, m), 7.12–7.51 (6H, m), 7.51–7.82 (8H, m), 7.97 (1H, d, J=8 Hz), 8.64 (1H, d, J=6 Hz), 8.70 (2H, d, J=6 Hz), 8.80 (1H, s-like)

Example 4

The following compounds were obtained according to a similar manner to that of Example 3-(3).

(1) 8-[2,6-Dichloro-3-[N-[4-(dimethylcarbamoyl)-cinnamoylglycyl]-N-methylamino]benzyloxy]-2-methyl-4-(2-pyridylmethoxy)quinoline (from 8-[3-(N-glycyl-N-methylamino)-2,6-dichlorobenzyloxy]-2-methyl-4-(2-pyridylmethoxy)quinoline and 4-(dimethylcarbamoyl) cinnamic acid).

NMR (CDCl$_3$, δ): 2.64 (3H, s), 2.98 (3H, br s), 3.10 (3H, br s), 3.25 (3H, s), 3.61 (1H, dd, J=4, 18 Hz), 3.91 (1H, dd, J=4, 18 Hz), 5.40 (2H, s), 5.64 (1H, s-like), 6.51 (1H, d, J=16 Hz), 6.71 (1H, s), 6.75 (1H, t-like), 7.21–7.35 (3H, m), 7.35–7.45 (3H, m), 7.45–7.64 (5H, m), 7.76 (1H, t, J=8 Hz), 7.96 (1H, d, J=8 Hz), 8.65 (1H, d, J=6 Hz)

(2) 8-[2,6-Dichloro-3-[N-[3-methoxy-4-(methylcarbamoyl)cinnamoylglycyl]-N-methylamino] benzyloxy]-2-methyl-4-(2-pyridylmethoxy)quinoline (from 8-[3-(N-glycyl-N-methylamino)-2,6-dichlorobenzyloxy]-2-methyl-4-(2-pyridylmethoxy)quinoline and 3-methoxy-4-(methylcarbamoyl)-cinnamic acid).

NMR (CDCl$_3$, δ): 2.65 (3H, s), 3.01 (3H, d, J=6 Hz), 3.27 (3H, s), 3.64 (1H, dd, J=4, 18 Hz), 3.87–3.98 (4H, m), 5.40 (2H, s), 5.63 (2H, s-like), 6.54 (1H, d, J=6 Hz), 6.68–6.76 (2H, m), 7.04 (1H, s), 7.21 (1H, d, J=8 Hz), 7.23–7.34 (3H, m), 7.41 (1H, t, J=8 Hz), 7.45–7.55 (2H, m), 7.60 (1H, d, J=8 Hz), 7.71–7.83 (2H, m), 7.96 (2H, d, J=8 Hz), 8.21 (1H, d, J=8 Hz), 8.64 (1H, d, J=6 Hz)

(3) 8-[2,6-Dichloro-3-[N-methyl-N-[4-(4-pyridylcarbamoyl)-cinnamoylglycyl]amino]benzyloxy]-2-methyl-4-(2-pyridylmethoxy)quinoline (from 8-[3-(N-glycyl-N-methylamino)-2,6-dichlorobenzyloxy]-2-methyl-4-(2-pyridylmethoxy)quinoline and 4-(4-pyridylcarbamoylcinnamic acid).

NMR (CDCl$_3$, δ): 2.52 (3H, s), 3.18 (3H, s), 3.60 (1H, dd, J=4, 18 Hz), 3.85 (1H, dd, J=4, 18 Hz), 5.41 (2H, s), 5.57 (2H, s), 6.48 (1H, d, J=16 Hz), 6.63–6.82 (2H, m), 7.17–7.55 (6H, m), 7.55–7.70 (5H, m), 7.78 (2H, td, J=8 Hz), 7.81 (2H, d, J=8 Hz), 7.97 (1H, d, J=8 Hz), 8.47 (2H, d, J=6 Hz), 8.63 (1H, d, J=6 Hz), 9.07 (1H, s)

(4) 8-[2,6-Dichloro-3-[N-methyl-N-[4-(2-oxopyrrolidin-1-yl)cinnamoylglycyl]amino]benzyloxy]-2-methyl-4-(2-pyridylmethoxy)quinoline (from 8-[3-(N-glycyl-N-methylamino)-2,6-dichlorobenzyloxy]-2-methyl-4-(2-pyridylmethoxy)quinoline and 4-(2-oxopyrrolidin-1-yl) cinnamic acid).

NMR (CDCl$_3$, δ): 2.10–2.25 (2H, m), 2.63 (2H, t, J=7.5 Hz), 2.66 (3H, s), 3.25 (3H, s), 3.61 (1H, dd, J=4, 18 Hz), 3.83–3.99 (3H, m), 5.41 (2H, s), 5.64 (2H, s), 6.43 (1H, d, J=16 Hz), 6.63 (1H, br peak), 6.71 (1H, s), 7.23–7.35 (3H, m), 7.41 (1H, t, J=8 Hz), 7.45–7.70 (7H, m), 7.76 (1H, td, J=8, 2 Hz), 7.96 (1H, d, J=8 Hz), 8.65 (1H, d, J=6 Hz)

(5) 8-[2,6-Dichloro-3-[N-methyl-N-[(E)-3-[6-[(E)-2-(pyridin-4-yl)vinyl pyridin-3-yl]acryloylglycyl]amino] benzyloxy]-2-methyl-4-(2-pyridylmethoxy)quinoline (from 8-[3-(N-glycyl-N-methylamino)-2,6-dichlorobenzyloxy]-2-methyl-4-(2-pyridylmethoxy)quinoline and (E)-3-[6-l(E)-2-(pyridin-4-yl)vinyl]pyridin-3-yl]acrylic acid).

NMR (CDCl$_3$, δ): 2.65 (3H, s), 3.28 (3H, s), 3.65 (1H, dd, J=4, 18 Hz), 3.94 (1H, dd, J=4, 18 Hz), 5.41 (2H, s), 5.64 (2H, s-like), 7.23–7.45 (8H, m), 7.49 (1H, d, j=8 Hz), 7.53–7.67 (3H, m), 7.75 (1H, d, J=8 Hz), 7.81 (1H, d, J=8 Hz), 7.96 (1H, d, J=8 Hz), 8.59–8.67 (3H, m), 8.73 (1H, s-like)

Example 5

(1) 8-[2,6-Dichloro-3-[N-[(E)-3-(6-ethoxycarbonylpyridin-3-yl)acryloylglycyl]-N-methylamino]benzyloxy]-2-methyl-4-(2-pyridylmethoxy) quinoline was obtained from 8-[3-(N-glycyl-N-methylamino)-2,6-dichlorobenzyloxy]-2-methyl-4-(2-pyridylmethoxy)quinoline and (E)-3-(6-ethoxycarbonylpyridin-3-yl)acrylic acid according to a similar manner to that of Example 3-(3).

NMR (CDCl$_3$, δ): 1.45 (1H, t, J=8 Hz), 2.65 (3H, s), 3.26 (3H, s), 3.66 (1H, dd, J=4, 18 Hz), 3.93 (1H, dd, J=4, 18 Hz), 4.50 (2H, q, J=7.5 Hz), 5.41 (2H, s), 5.65 (2H, s), 6.66 (1H, d, J=16 Hz), 6.72 (1H, s), 6.83 (1H, br peak), 7.23–7.44 (3H, m), 7.41 (1H, td, J=8, 2 Hz), 7.50 (1H, d, J=8 Hz), 7.56–7.64 (2H, m), 7.76 (1H, t, J=8 Hz), 7.87–7.98 (2H, m), 8.12 (1H, d, J=8 Hz), 8.62–8.67 (1H, m), 8.83 (1H, s-like)

(2) To a solution of 8-[2,6-dichloro-3-[N-[(E)-3-(6-ethoxycarbonylpyridin-3-yl)acryloylglycyl]-N-methylamino]benzyloxy]-2-methyl-4-(2-pyridylmethoxy) quinoline (30 mg) in ethanol (0.5 ml) was added 1N aqueous sodium hydroxide solution (0.1 ml) at ambient temperature, and the mixture was stirred at 50° C. for 6 hours. The reaction mixture was evaporated in vacuo, and the residue was dissolved in water. The aqueous layer was washed with diethyl ether and adjusted to pH 5 with 1N hydrochloric acid. The precipitate was collected by filtration to give 8-[3-[N-[(E)-3-(6-carboxypyridin-3-yl)acryloylglycyl]-N-methylamino]- 2,6-dichlorobenzyloxy]-2-methyl-4-(2-pyridylmethoxy)quinoline (28 mg) as powder.

NMR (DMSO-d$_6$, δ): 2.55 (3H, s), 3.15 (3H, s), 3.47–3.58 (1H, m), 3.77–3.90 (1H, m), 5.43 (2H, s), 5.46–5.57 (2H, m), 6.98 (1H, d, J=16 Hz), 7.08 (1H, s), 7.34–7.95 (9H, m), 8.03–8.53 (3H, m), 8.53–8.65 (2H, m)

(3) To a solution of 8-[3-[N-[(E)-3-(6-carboxypyridin-3-yl)acryloylglycyl]-N-methylamino]-2,6-dichlorobenzyloxy]-2-methyl-4-(2-pyridylmethoxy) quinoline (25 mg) and methylamine hydrochloride (3 mg) in N,N-dimethylformamide (2 ml) were added 1-ethyl-3-(3-dimethylaminopropyl)carbodiimide hydrochloride (7 mg) and 1-hydroxybenzotriazole (7 mg) at ambient temperature, and the mixture was allowed to stand for 1 day at ambient temperature. The reaction mixture was poured into water and extracted with chloroform. The organic layer was washed with water and aqueous sodium hydrogen carbonate solution, dried over magnesium sulfate and evaporated in vacuo. The residue was purified by preparative thin layer chromatography (chloroform:methanol=10:1, V/V) to give 8-[2,6-dichloro-3-[N-methyl-N-[(E)-3-[6-(methylcarbamoyl)pyridin-3-yl]acryloylglycyl]amino]-benzyloxy]-2-methyl-4-(2-pyridylmethoxy)quinoline (5 mg) as an oil.

NMR (CDCl$_3$, δ): 2.66 (3H, s), 3.04 (3H, d, J=6 Hz), 3.26 (3H, s), 3.65 (1H, dd, J=4, 18 Hz), 3.93 (1H, dd, J=4, 18 Hz), 5.41 (2H, s), 5.65 (2H, s-like), 6.63 (1H, d, J=16 Hz), 6.72 (1H, s), 6.80 (1H, br peak), 7.24–7.35 (3H, m), 7.40 (1H, t, J=8 Hz), 7.48 (1H, d, J=8 Hz), 7.56–7.65 (2H, m), 7.76 (1H, t, J=8 Hz), 7.89–8.00 (3H, m), 8.18 (1H, d, J=8 Hz), 8.59–8.68 (2H, m)

its trihydrochloride

NMR (CD$_3$OD, δ): 2.99 (3H, s), 3.23–3.33 (3H, m, overlapped with CH$_3$OD), 3.85 (1H, d, J=18 Hz), 4.03 (1H, d, J=18 Hz), 5.70 (1H, d, J=10 Hz), 5.80 (1H, d, J=10 Hz), 6.05 (2H, s), 6.96 (1H, d, J=16 Hz), 7.60 (1H, br d), 7.68–7.77 (2H, m), 7.82–7.95 (3H, m), 8.10–8.28 (3H, m), 8.34–8.45 (2H, m), 8.75 (1H, t, J=8 Hz), 8.86 (1H, br peak), 9.03 (1H, d, J=6 Hz)

Example 6

(1) 8-[3-[N-[(E)-3-(6-Aminopyridin-3-yl)acryloylglycyl]-N-methylamino]-2,6-dichlorobenzyloxy]-2-methyl-4-(2-pyridylmethoxy)quinoline was obtained from 8-[3-(N-glycyl-N-methylamino)-2,6-dichlorobenzyloxy]-2-methyl-4-(2-pyridylmethoxy)quinoline and (E)-3-(6-aminopyridin-3-yl)acrylic acid according to a similar manner to that of Example 3-(3).

NMR (CDCl$_3$, δ): 2.66 (3H, s), 3.26 (3H, s), 3.63 (1H, dd, J=4, 18 Hz), 3.92 (1H, dd, J=4, 18 Hz), 4.70 (2H, s), 5.41 (2H, s), 5.63 (2H, s), 6.30 (1H, d, J=16 Hz), 6.48 (1H, d, J=8 Hz), 6.61 (1H, t-like), 6.71 (1H, s), 7.22–7.54 (6H, m), 7.60 (2H, d, J=8 Hz), 7.77 (1H, td, J=8, 2 Hz), 7.97 (1H, dd, J=8, 2 Hz), 8.17 (1H, d, J=2 Hz), 8.64 (1H, d, J=6 Hz)

(2) To a mixture of 8-[3-[N-[(E)-3-(6-aminopyridin-3-yl)acryloylglycyl]-N-methylamino]-2,6-dichlorobenzyloxy]-2-methyl-4-(2-pyridylmethoxy)quinoline (90 mg), triethylamine (56 mg) and dichloromethane (2 ml) was added 4-pyridylacetyl chloride hydrochloride (53 mg) in ice water bath under nitrogen atmosphere, and the mixture was stirred for 1 hour at the same temperature and allowed to stand for 1 day at ambient temperature. The reaction mixture was poured into water and extracted with chloroform. The organic layer was washed with water and brine, dried over magnesium sulfate and evaporated in vacuo. The residue was purified by preparative thin layer chromatography (chloroform:methanol=10:1, V/V) to give 8-[2,6-dichloro-3-[N-methyl-N-[(E)-3-[6-( 4-pyridylacetamnido) pyridin-3-yl] acryloylglycyl] amino]-benzyioxy]-2-methyl-4-(2-pyridylmethoxy) quinoline (10 mg) as an amorphous powder.

NMR (CDCl$_3$, δ): 2.65 (3H, s), 3.25 (3H, s), 3.63 (1H, dd, J=4, 18 Hz), 3.74 (2H, s), 3.93 (1H, dd, J=4, 18 Hz), 5.41 (2H, s), 5.63 (2H, s-like), 6.46 (1H, d, J=16 Hz), 6.71 (1H, s), 6.75 (1H, br peak), 7.24–7.33 (5H, m), 7.34 (1H, t, J=8 Hz), 7.40–7.55 (2H, m), 7.59 (1H, d, J=8 Hz), 7.75 (1H, t, J=8 Hz), 7.81 (1H, d, J=8 Hz), 7.95 (1H, d, J=8 Hz), 8.12–8.21 (2H, m), 8.31 (1H, d, J=2 Hz), 8.59–8.67 (3H, m)

Example 7

8-[2,6-Dichloro-3-[N-mnethyl-N-[(E)-3-[6-(2-methylnicotinamido)pyridin-3-yl]acryloylglycyl]amino]-benzyloxy]-2-methyl-4-(2-pyridylmnethoxy) quinoline was obtained by reacting [3-[N-[(E)-3-(6-aminopyridin-3-yl) acryloyiglycyl]-N-methylamino]-2, 6-dichlorobenzyloxy]-2-methyl-4-(2-pyridylmethoxy) quinoline with 2-methylnicotinoyl chloride hydrochloride according to a similar manner to that of Example 6-(2)

NMR (CDCl$_3$, δ): 2.65 (3H, s), 2.75 (3H, s), 3.25 (3H, s), 3.64 (1H, dd, J=4, 18 Hz), 3.93 (1H, dd, J=4, 18 Hz), 5.40 (2H, s), 5.65 (1H, s-like), 6.50 (1H, d, J=16 Hz), 6.72 (1H, s), 6.79 (1H, br peak), -7.17–7.35 (4H, in), 7.35–7.63 (4H, mn), 7.77 (1H, t, J=8 Hz), 7.86 (1H, d, J=8 Hz), 7.89 (1H, d, J=8 Hz), 7.96 (1H, d, J=8 Hz), 8.29 (1H, s-like), 8.37 (1H, d, J=8 Hz), 8.55–8.70 (3H, m)

Example 8

A mixture of 8-[3-(N-glycyl-N-methylamino)-2,6-dichlorobenzyloxy]-2-methyl-4-(2-pyridylmethoxy) quinoline (35 mg), phenyl 3-[N-(4-pyridyl) carbamoyl] phenylcarbamate (24 mg) and triethylamine (13.9 mg) in N,N-dimethylformnamide (1 ml) was stirred for 2 hours at 80° C. The mixture was poured into water and extracted with chloroform. The organic layer was washed with water and brine, dried over magnesium sulfate and evaporated in vacuo. The residue was purified by preparative thin layer chromatography (chloroform:methanol=10:1, V/V) to give 8-[2,6-dichloro-3-[N-methyl-N-[N'-[3-[N-(4-pyridyl)-carbamoyl]phenyl]ureidoacetyl]amino]benzyloxy]-2-methyl-4-(2-pyridylmethoxy)quinoline (15 mg) as amorphous powder.

NMR (CDCl$_3$, δ): 2.52 (3H, s), 3.17 (3H, s), 3.73-3.99 (2H, m), 5.31–5.43 (3H, m), 5.49 (1H, d, J=10 Hz), 6.43 (1H, br peak), 6.70 (1H, s), 6.93–7.05 (2H, m), 7.12–7.36 (4H, m), 7.40–7.50 (2H, m), 7.50–7.70 (2H, m), 7.76 (1H, td, J=8, 2 Hz), 7.85 (2H, d, J=6 Hz), 7.97 (1H, d, J=8 Hz), 8.34–8.59 (3H, m), 8.63 (1H, d, J=6 Hz), 9.70 (1H, br s)

Example 9

To a solution of 4-[3-[N-[(E)-3-(6-acetamidopyridin-3-yl) acryloylglycyl]-N-methylamino]-2,6-dichlorobenzyloxy]-2-methoxy-1H-benzimidazole (100 mg) and 2-chloromethylpyridine hydrochloride (29 mg) in N,N-dimethylformamide (2 ml) was added potassium carbonate (93 mg) at ambient temperature, and the mixture was stirred for 28 hours at the same temperature. The reaction mixture was poured into water and extracted with chloroform. The organic layer was separated, washed with water and brine, dried over magnesium sulfate and evaporated in vacuo. The residue was purified by preparative thin layer chromatography (ethyl acetate:methanol=12:1, V/V; chloroform:methanol=12:1, V/V) to give 4-[3-[N-[(E)-3-(6-acetamidopyridin-3-yl)acryloylglycyl]-N-methylamino]-2,6-dichlorobenzyloxy]-2-methoxy-1-(2-pyridylmethyl)-1H-benzimidazole (50 mg) as an amorphous powder.

NMR (CDCl$_3$, δ): 2.21 (3H, s), 3.25 (3H, s), 3.66 (1H, dd, J=4, 18 Hz), 3.95 (1H, dd, J=4, 18 Hz), 4.22 (3H, s), 5.27 (2H, s), 5.67 (2H, s), 6.45 (1H, d, J=16 Hz), 5.67 (1H, t-like), 6.76–6.88 (2H, m), 6.92 (1H, d, J=8 Hz), 7.20 (1H, dd, J=6, 8 Hz), 7.31 (1H, d, J=8 Hz), 7.45–7.63 (3H, m), 7.84 (1H, dd, J=2, 8 Hz), 8.19–8.29 (2H, m), 8.34 (1H, d, J=2 Hz), 8.59 (1H, d, J=5 Hz)

Example 10

The following compounds were obtained according to a similar manner to that of Example 9.

(1) 4-[3-[N-[(E)-3-(6-Acetamidopyridin-3-yl)acryloylglycyl]-N-methylamino]-2,6-dichlorobenzyloxy]-2-methoxy-1-benzyl-1H-benzimidazole (from 4-[3-[N-[(E)-3-(6-acetamidopyridin-3-yl)-acrvioylglycyl]-N-methylamino]-2,6-dichlorobenzyloxy]-2-methoxy-1H-benzimidazole and benzyl bromide).

NMR (CDCl$_3$, δ): 2.21 (3H, s), 2.28 (3H, s), 3.65 (1H, dd, J=17, 4 Hz), 3.94 (1H, dd, J=17, 5 Hz), 4.21 (3H, s), 5.13 (2H, s), 5.67 (2H, s), 6.45 (1H, d, J=15 Hz), 6.68 (1H, br t, J=5 Hz), 6.79 (1H, d, J=7.5 Hz), 6.82 (1H, d, J=7.5 Hz), 7.05 (1H, t, J=7.5 Hz), 7.20 (2H, br d, J=7.5 Hz), 7.27–7.36 (4H, m), 7.49 (1H, d, J=7.5 Hz), 7.51 (1H, d, J=15 Hz), 7.84 (1H, br d, J=7.5 Hz), 8.11 (1H, br s), 8.20 (1H, br d, J=7.5 Hz), 8.35 (1H, br s)

(2) 4-[3-[N-[(E)-3-(6-Acetamidopyridin-3-yl)-acryloylglycyl]-N-methylamino]-2,6-dichlorobenzyloxy]-1-ethoxycarbonylmethyl-2-methoxy-1H-benzimidazole (from 4-[3-[N-[(E)-3-(6-acetamidopyridin-3-yl) acryloylglycyl]-N-methylamino]-2,6-dichlorobenzyloxy]-2-methoxy-1H-benzimidazole and ethyl bromoacetate).

NMR (CDCl$_3$, δ): 1.27 (3H, t, J=7 Hz), 2.20 (3H, s), 3.28 (3H, s), 3.65 (1H, m), 3.95 (1H, m), 4.20 (2H, s), 4.24 (2H, q, J=8 Hz), 4.68 (2H, s), 5.66 (2H, s), 6.47 (1H, d, J=15 Hz), 6.70 (1H, br), 6.77 (1H, d, J=8 Hz), 6.86 (1H, d, J=8 Hz), 7.10 (1H, t, J=8 Hz), 7.30 (1H, d, J=8 Hz), 7.48–7.56 (2H, m), 7.83 (1H, m), 8.15–8.22 (2H, m), 8.35 (1H, m)

Example 11

8-[3-[N-(Acetylglycyl)-N-methylamino]-2,6-dichlorobenzyloxy]- 2-methyl-4-(2-pyridylmethoxy) quinoline was obtained by reacting 8-[3-(N-glycyl-N-methylamino)-2,6-dichlorobenzyloxy]-2-methyl-4-(2-pyridylmethoxy)quinoline with acetic anhydride.

Example 12

8-[2,6-dimethyl-3-[N-[4-(methylcarbamoyl) cinnamoylglycyl]-N-methylamino]benzyloxy]-2-methyl-4-(2-pyridylmethoxy)quinoline is obtained by reacting 8-hydroxy-2-methyl-4-(2-pyridylmethoxy)quinoline with 2,6-dimethyl-3-[N-[4-(methylcarbamoyl)cinnamoylglycyl]-N-methylamino]benzyl chloride according to a similar manner to that of Example 1-(2).

Example 13

(1) To a solution of 3-(tert-butyldiphenylsilyloxymethyl)-2,4-dichloroaniline (6.08 g) in acetic acid (15 ml) was added 2,5-dimethoxytetrahydrofuran (1.87 g). The mixture was stirred at 90° C. for 1 hour and evaporated under reduced pressure. The residue was purified by a silica gel column chromatography eluted with n-hexane—ethyl acetate to give 1-[3-(tert-butyldiphenylsilyloxymethyl)-2,4-dichlorophenyl]pyrrole (5.82 g) as a pale yellow oil.

NMR (CDCl$_3$, δ): 1.06 (9H, s), 4.98 (2H, s), 6.32 (2H, d, J=4 Hz), 6.83 (2H, d, J=4 Hz), 7.22 (1H, d, J=10 Hz), 7.32–7.48 (7H), 7.74 (4H, d, J=8 Hz) (2) To a solution of 1-[3-(tert-butyldiphenylsilyloxymethyl)-2,4-dichlorophenyl]pyrrole (1.20 g) in anhydrous dichloromethane (12 ml) was added a solution of chlorosulfonyl isocyanate (0.28 ml) in anhydrous dichloromethane (2.8 ml) dropwise in a dry ice-carbon tetrachloride bath. The mixture was stirred at the same temperature for 30 minutes and then at ambient temperature for additional 1 hour. Anhydrous dimethylformamide (0.4 ml) was added to this mixture dropwise in a dry ice-carbon tetrachloride bath. After stirring at the same temperature for 30 minutes and at ambient temperature for additional 1 hour, the reaction mixture was treated with 4N-hydrochloric acid under ice-water cooling for 30 minutes. The organic layer was isolated and the aqueous layer was extracted with chloroform twice. The combined organic phases were washed with saturated aqueous sodium hydrogen carbonate, dried over magnesium sulfate and evaporated in vacuo. The residue was purified by a silica gel column chromatography eluted with n-hexane—ethyl acetate to give 1-[3-(tert-butyldiphenylsilyloxymethyl)-2,4-dichlorophenyl]-2-cyanopyrrole (930 mg) as a pale yellow oil.

NMR (CDCl$_3$, δ): 1.07 (9H, s), 4.98 (2H, s), 6.38 (1H, t, J=4 Hz), 6.93 (1H, d, J=4 Hz), 6.98 (1H, d, J=4 Hz), 7.31 (1H, d, J=8 Hz), 7.33–7.48 (7H), 7.68–7.77 (4H)

(3) To a solution of 1-[3-(tert-butyldiphenylsilyloxymethyl)-2,4-dichlorophenyl]-2-cyanopyrrole (820 mg) in anhydrous tetrahydrofuran (16 ml) was added lithium aluminum hydride (74 mg) and the mixture was stirred at ambient temperature for 1 hour. The reaction mixture was quenched by adding water (2 ml) dropwise under ice-water cooling. Ethyl acetate (50 ml) and water (50 ml) were added thereto and the precipitate was filtered off. The organic layer was isolated and the aqueous layer was extracted with ethyl acetate. The combined organic phases were washed with brine, dried over magnesium sulfate and evaporated in vacuo. The residue was purified by a silica gel column chromatography eluted with chloroform-methanol to give 2-aminomethyl-1-[3-(tert-butyldiphenylsilyloxymethyl)-2,4-dichlorophenyl]pyrrole (414 mg) as a pale yellow oil.

NMR (CDCl$_3$, δ): 1.06 (9H, s), 3.52 (1H, d, J=15 Hz), 3.63 (1H, d, J=15 Hz), 4.97 (2H, s), 6.19–6.30 (2H), 6.63 (1H, d, J=4 Hz), 7.30 (1H, d, J=8 Hz), 7.34–7.48 (7H), 7.68–7.79 (4H)

(4) To a solution of 2-aminomethyl-1-[3-(tert-butyldiphenylsilyloxymethyl)-2,4-dichlorophenyl]pyrrole (465 mg) in anhydrous dimethylformamide (7 ml) were added 4-(methylcarbamoyl)cinnamic acid (206 mg), 1-ethyl-3-(3-dimethylaminopropyl)carbodiimide hydrochloride (219 mg) and 1-hydroxybenzotriazole (185 mg). The mixture was stirred at ambient temperature for 3 hours and partitioned between ethyl acetate and water. The organic layer was isolated and the aqueous layer was extracted with ethyl acetate. The organic layers were combined, washed with saturated aqueous sodium hydrogen carbonate and brine, dried over magnesium sulfate and evaporated in vacuo. The residue was triturated with diisopropyl ether to give 1-[3-(tert-butyldiphenylsilyloxymethyl)-2,4-dichlorophenyl]-2-[4-(methylcarbamoyl) cinnamoylaminomethyl]pyrrole (622 mg) as a brownish powder.

NMR (CDCl$_3$, δ): 1.02 (9H, s), 3.02 (3H, d, J=6 Hz), 4.32 (2H, d, J=6 Hz), 4.88 (2H, s), 5.62 (1H, t-like), 6.10 (1H, br s), 6.24 (1H, d, J=16 Hz), 6.27–6.32 (2H), 6.68 (1H, d, J=4 Hz), 7.23–7.50 (11H), 7.64–7.74 (6H)

(5) To a solution of 1-[3-(tert-butyldiphenylsilyloxymethyl)-2,4-dichlorophenyl]-2-[4-(methylcarbamoyl)cinnamoylaminomethyl]pyrrole (620 mg) in tetrahydrofuran (6 ml) was added 1H solution of tetrabutylammonium fluoride in tetrahydrofuran (2.5 ml). The mixture was stirred at ambient temperature for 6 hours and partitioned between ethyl acetate and water. The organic layer was isolated and the aqueous layer was extracted with ethyl acetate. The combined organic layers were washed with 1N hydrochloric acid and brine, dried over magnesium sulfate and evaporated in vacuo. The residue was triturated with methanol to give 1-(2,4-dichloro-3-hydroxymethylphenyl)-2-[4-(methylcarbamoyl) cinnamoylaminomethyl]pyrrole (197 mg) as a brownish powder.

NMR (DMSO-d$_6$, δ): 2.79 (3H, d, J=6 Hz), 4.06 (1H, dd, J=16, 6 Hz), 4.21 (1H, dd, J=16, 6 Hz), 4.70 (2H, d, J=6 Hz), 5.30 (1H, t, J=6 Hz), 6.16–6.23 (2H), 6.64 (1H, d, J=16 Hz), 6.76 (1H, br s), 7.34 (1H, d, J=16 Hz) 7.46 (1H, d, J=8 Hz), 7.53–7.63 (3H), 7.86 (2H, d, J=8 Hz), 8.28 (1H, t-like), 8.48 (1H, br s)

(6) To a mixture of 1-(2,4-dichloro-3-hydroxymethylphenyl)-2-[4-(methylcarbamoyl) cinnamoylaminomethyl]pyrrole (148 mg), triethylamine (0.11 ml) and anhydrous dimethylformamide (1 ml) was added a 1M solution of methanesulfonyl chloride in dimethylformamide (0.77 ml) under ice-water cooling. The mixture was stirred at ambient temperature for 4 hours and partitioned between chloroform and saturated aqueous solution of sodium hydrogen carbonate. The organic layer was isolated, dried over magnesium sulfate and evaporated in vacuo to give a brown oil. The residue was purified by preparative thin layer chromatography (chloroform-methanol) to give 1-(2,4-dichloro-3-chloromethylphenyl)-2-[4-(methylcarbamoyl)cinnamoylaminomethyl]pyrrole (120 mg) as an amorphous powder.

NMR (CDCl$_3$-CD$_3$OD, $\delta$): 2.99 (3H, d, J=5 Hz), 4.28 (1H, d, J=16 Hz), 4.38 (1H, d, J=16 Hz), 4.86 (2H, s), 6.26–6.40 (4H), 6.69 (1H, br s), 6.83 (1H, br s), 7.34 (1H, d, J=8 Hz), 7.43 (1H, d, J=8 Hz), 7.50 (2H, d, J=8 Hz), 7.75 (2H, d, J=8 Hz)

(7) 1-[2,4-Dichloro-3-[2-methyl-4-(2-pyridylmethoxy) quinolin-8-yloxymethyl]phenyl]-2-[4-(methylcarbamoyl) cinnamoylaminomethyl]pyrrole is obtained by reacting 1-(2, 4-dichloro-3-chloromethylphenyl)-2-[4-(methylcarbamoyl) cinnamoylaminomethyl]pyrrole with 8-hydroxy-2-methyl-4-(2-pyridylmethoxy)quinoline according to a similar manner to that of Example 1-(2).

Example 14

(1) To a mixture of 1-(3-tert-butyldiphenylsilyloxymethyl-2,4-dichlorophenyl)-2-cyanopyrrole (900 mg) and silicic acid (100 mg) in carbon tetrachloride (15 ml) was added a solution of tert-butyl hypochlorite (222 mg) in carbon tetrachloride (10 ml) in water bath, and the mixture was stirred for 30 minutes at the same temperature. The reaction mixture was filtered, and the filtrate was evaporated in vacuo. The residue was purified by silica gel column chromatography eluting with a mixture of n-hexane and ethyl acetate (15:1, V/V) to give 1-(3-tert-butyldiphenylsilyloxymethyl-2,4-dichlorophenyl)-4-chloro-2-cyanopyrrole (290 mg) as an oil.

NMR (CDCl$_3$, $\delta$): 1.07 (9H, s), 4.98 (2H, s), 6.90 (2H, s), 7.30 (1H, d, J=8 Hz), 7.36–7.52 (7H, in), 7.75 (4H, d-like)

(2) 2-Aminomethyl-1-(3-tert-butyldiphenylsilyloxymethyl-2,4-dichlorophenyl)-4-chloropyrrole was obtained according to a similar manner to that of Example 13-(3).

NMR (CDCl$_3$, $\delta$): 3.43 (1H, br d, J=15 Hz), 3.57 (1H, br d, J=15 Hz), 4.55 (2H, s), 6.16 (1H, s-like), 6.56 (1H, d, J=2 Hz), 7.26 (1H, d, J=8 Hz), 7.33–7.48 (7H, m), 7.72 (4H, d-like)

(3) 1-(3-tert-Butyldiphenylsilyloxymethyl-2,4-dichlorophenyl)-2-[4-(methylcarbamoyl) cinnamoylaminomethyl]- 4-chloropyrrole was obtained according to a similar manner to that of Example 13-(4).

NMR (CDCl$_3$, $\delta$): 1.03 (9H, s), 3.02 (3H, d, J=6 Hz), 4.24 (2H, d, J=6 Hz), 4.87 (2H, s), 5.60 (1H, t-like), 6.07 (1H, br peak), 6.20–6.29 (2H, m), 6.63 (1H, d, J=2 Hz), 7.21–7.27 (1H, m), 7.30–7.51 (10H, m), 7.64–7.73 (6H, m)

(4) 4-Chloro-1-(2,4-dichloro-3-hydroxymethylphenyl)-2-[4-(methylcarbamoyl)cinnamoylaminomethyl]pyrrole was obtained according to a similar manner to that of Example 13-(5).

NMR (DMSO-d$_6$, $\delta$): 2.78 (3H, d, J=6 Hz), 3.94–4.06 (1H, m), 4.06–4.18 (1H, m), 4.20 (2H, d, J=6 Hz), 5.33 (1H, t-like), 6.24 (1H, d, J=2 Hz), 6.61 (1H, d, J=16 Hz), 6.98 (1H, d, J=2 Hz), 7.34 (1H, d, J=16 Hz), 7.48(1H, d, J=8 Hz), 7.55–7.63 (3H, m), 7.85 (2H, d, J=8 Hz), 8.32 (1H, t-like), 8.46 (1H, q-like)

(5) 4-Chloro-1-(2,4-dichloro-3-chloromethylphenyl)-2-[4-(methylcarbamoyl)cinnamoylaminomethyl]pyrrole was obtained according to a similar manner to that of Example 13-(6).

NMR (CDCl$_3$-CD$_3$OD, $\delta$): 3.00 (3H, s), 4.22 (1H, d, J=15 Hz), 4.31 (1H, d, J=15 Hz), 4.85 (2H, s), 6.27 (1H, s-like), 6.34 (1H, d, J=16 Hz), 6.64 (1H, d, J=2 Hz), 7.33 (1H, d, J=8 Hz), 7.41–7.56 (4H, m), 7.74 (2H, d, J=8 Hz)

(6) 4-Chloro-1-[2,4-dichloro-3-[2-methyl-4-(2-pyridylmethoxy)quinolin-8-yloxymethyl]phenyl]-2-[4-(methylcarbamoyl)cinnamoylaminomethyl]pyrrole is obtained according to a similar manner to that of Example 1-(2).

Example 15

(1) To a solution of 1-(3-tert-butyldiphenylsilyloxymethyl-2,4-dichlorophenyl)pyrrole (1.0 g) in tetrahydrofuran (10 ml) was added N-chlorosuccinimide (292 mg) at ambient temperature, and the mixture was allowed to stand for 1 day. The reaction mixture was poured into water and extracted with ethyl acetate. The organic layer was washed with water and brine, dried over magnesium sulfate and evaporated in vacuo. The residue was chromatographed on silica gel eluting with a mixture of n-hexane and ethyl acetate (10:1, V/V) to give 1-(3-tert-butyldiphenylsilyloxymethyl-2,4-dichlorophenyl)-2-chloropyrrole (1.0 g) as an oil.

NMR (CDCl$_3$, $\delta$): 1.04 (9H, s), 4.48 (2H, s), 6.17–6.23 (1H, m), 6.26–6.31 (1H, m), 6.63–6.69 (1H, m), 7.20–7.27 (1H, m), 7.33–7.49 (7H, m), 7.69–7.79 (4H, m)

(2) 1-(3-tert-Butyldiphenylsilyloxymethyl-2,4-dichlorophenyl)-5-chloro-2-cyanopyrrole was obtained according to a similar manner to that of Example 13-(2).

NMR (CDCl$_3$, $\delta$): 1.05 (9H, s), 4.98 (2H, s-like), 6.30 (1H, d, J=4 Hz), 6.95 (1H, d, J=4 Hz), 7.30 (1H, d, J=8 Hz), 7.35–7.50 (7H, m), 7.73 (4H, d-like)

(3) 2-Aminomethyl-1-(3-tert-butyldiphenylsilyloxymethyl-2,4-dichlorophenyl)-5-chloropyrrole was obtained according to a similar manner to that of Example 13-(3).

NMR (CDCl$_3$, $\delta$): 1.04 (9H, s), 3.45 (1H, d, J=15 Hz), 3.55 (1H, d, J=15 Hz), 4.94 (2H, s), 6.12–6.20 (2H, m), 7.27 (1H, d, J=8 Hz), 7.32–7.48 (7H, m), 7.72 (4H, d-like)

(4) 1-(3-tert-Butyldiphenylsilyloxymethyl-2,4-dichlorophenyl)-2-[4-(methylcarbamoyl) cinnamoylaminomethyl]-5-chloropyrrole was obtained according to a similar manner to that of Example 13-(4).

NMR (CDCl$_3$, $\delta$): 1.00 (9H, s), 3.02 (3H, d, J=6 Hz), 4.26 (2H, d, J=6 Hz), 4.83 (1H, d, J=10 Hz), 4.90 (1H, d, J=10 Hz), 5.60 (1H, t-like), 6.08 (1H, q-like), 6.16–6.29 (3H, m), 7.23–7.30 (1H, m), 7.30–7.50 (10H, m), 7.64–7.73 (6H, m)

(5) 5-Chloro-1-(2,4-dichloro-3-hydroxymethylphenyl)-2-[4-(methylcarbamoyl)cinnamoylaminomethyl]pyrrole was obtained according to a similar manner to that of Example 13-(5).

NMR (DMSO-d$_6$, $\delta$): 2.78 (3H, d, J=6 Hz), 3.97 (1H, dd, J=4, 15 Hz), 4.16 (1H, dd, J=4, 15 Hz), 4.68 (2H, d, J=7 Hz), 5.35 (1H, t-like), 6.26 (2H, s-like), 6.61 (1H, d, J=16 Hz), 7.31 (1H, d, J=16 Hz), 7.49 (1H, d, J=8 Hz), 7.55–7.65 (3H, m), 7.85 (2H, d, J=8 Hz), 8.27 (1H, t-like), 8.48 (1H, q-like)

(6) 5-Chloro-1-(2,4-dichloro-3-chloromethylphenyl)-2-[4-(methylcarbamoyl)cinnamoylaminomethyl]pyrrole was obtained according to a similar manner to that of Example 13-(6).

NMR (CDCl$_3$-CD$_3$OD, δ): 3.00 (3H, s), 4.21 (1H, d, J=16 Hz), 4.35 (1H, d, J=16 Hz), 4.84 (2H, s), 6.11 (1H, t-like), 6.18 (1H, d, J=4 Hz), 6.28 (1H, d, J=4 Hz), 6.31 (1H, d, J=16 Hz), 6.60 (1H, q-like), 7.32 (1H, d, J=8 Hz), 7.41–7.54 (4H, m), 7.74 (2H, d, J=8 Hz)

(7) 5-Chloro-1-[2,4-dichloro-3-[2-methyl-4-(2-pyridylmethoxy)quinolin-8-yloxymethyl]phenyl]-2-[4-(methylcarbamoyl)cinnamoylaminomethyl]pyrrole is obtained according to a similar manner to that of Example 1-(2).

Example 16

(1) 1-(3-tert-Butyldiphenylsilyloxymethyl-4-chlorophenyl)pyrrole was obtained by reacting 3-(tert-butyldiphenylsilyloxymethyl)-4-chloroaniline with 2,5-dimethoxytetrahydrofuran according to a similar manner to that of Example 13-(1).

NMR (CDCl$_3$, δ): 1.14 (9H, s), 4.85 (2H, s), 6.35–6.40 (2H, m), 7.07–7.12 (2H, m), 7.21 (1H, dd, J=8, 2 Hz), 7.31 (1H, d, J=8 Hz), 7.34–7.49 (6H, m), 7.70 (4H, d-like), 7.82 (1H, d, J=2 Hz) (2) 1-(3-tert-Butyldiphenylsilyloxymethyl-4-chlorophenyl)-2-cyanopyrrole was obtained according to a similar manner to that of Example 13-(2).

NMR (CDCl$_3$, δ): 1.13 (9H, s), 4.84 (2H, s), 6.34–6.40 (1H, m), 7.00–7.04 (1H, m), 7.04–7.08 (1H, m), 7.28–7.50 (8H, m), 7.63–7.74 (4H, m), 7.78–7.84 (1H, m)

(3) 2-Aminomethyl-1-(3-tert-butyldiphenylsilyloxymethyl-4-chlorophenyl)pyrrole was obtained according to a similar manner to that of Example 13-(3).

NMR (CDCl$_3$, δ): 1.10 (9H, s), 3.85 (2H, s), 4.85 (2H, s), 6.21–6.30 (2H, m), 6.77–6.83 (1H, m), 7.21–7.29 (1H, m), 7.33–7.50 (7H, m), 7.69 (4H, d-like), 7.74–7.78 (1H, m)

(4) 1-(3-tert-Butyldiphenylsilyloxymethyl-4-chlorophenyl)-2-[4-(methylcarbamoyl)cinnamoylaminomethyl]pyrrole was obtained according to a similar manner to that of Example 13-(4).

NMR (CDCl$_3$, δ): 1.10 (9H, s), 3.01 (3H, d, J=6 Hz), 4.55 (2H, d, J=6 Hz), 4.83 (2H, s), 5.66 (1H, t-like), 6.13 (1H, q-like), 6.25–6.36 (3H, m), 6.80-6.85 (1H, m), 7.16 (1H, dd, J=8, 2 Hz), 7.33–7.50 (9H, m), 7.56 (1H, d, J=16 Hz), 7.63–7.75 (7H, m)

(5) 1–14-Chloro-3-hydroxymethylphenyl)-2-[4-(methylcarbamoyl)cinnamoylaminomethyl]pyrrole was obtained according to a similar manner to that of Example 13-(5).

NMR (DMSO-d$_6$, δ): 2.78 (3H, d, J=6 Hz), 4.31 (2H, d, J=6 Hz), 4.58 (2H, d, J=6 Hz), 5.49 (1H, t-like), 6.17–6.24 (2H, m), 6.20 (1H, d, J=16 Hz), 6.89–6.94 (1H, m), 7.33 (1H, dd, J=8, 2 Hz), 7.41 (1H, d, J=16 Hz), 7.47–7.55 (2H, m), 7.61 (2H, d, J=8 Hz), 7.85 (2H, d, J=8 Hz), 8.40–8.51 (2H, m)

(6) 1-(4-Chloro-3-chloromethylphenyl)-2-[4-(methylcarbamoyl)cinnamoylaminomethyl]pyrrole was obtained according to a similar manner to that of Example 13-(6).

NMR (DMSO-d$_6$, δ): 2.78 (3H, d, J=6 Hz), 4.34 (2H, d, J=6 Hz), 6.83 (2H, s), 6.17–6.26 (2H, m), 6.69 (1H, d, J=16 Hz), 6.93–6.98 (1H, m), 7.36–7.48 (2H, m), 7.55–7.70 (4H, m), 7.84 (2H, d, J=8 Hz), 8.40–8.51 (2H, m)

(7) 1-[4-Chloro-3-[2-methyl-4-(2-pyridylmethoxy)quinolin-8-yloxymethyl]phenyl]-2-[4-(methylcarbamoyl)

cinnamoylamino-methyl]pyrrole is obtained according to a similar manner to that of Example 1-(2).

Example 17

(1) To a mixture of 2-aminomethyl-1-(3-tert-butyldiphenylsilyloxymethyl-2,4-dichlorophenyl)pyrrole (87 mg) and pyridine (20.3 mg) in dichloromethane (1 ml) was added acetic anhydride (20.9 mg) under ice-cooling, and the mixture was stirred for 3 hours at ambient temperature. The mixture was poured into water and extracted with dichloromethane. The organic layer was washed with 1H hydrochloric acid, water, saturated sodium bicarbonate solution and brine, dried over magnesium sulfate and evaporated in vacuo to give 2-acetamidomethyl-1-(3-tert-butyldiphenylsilyloxymethyl-2,4-dichlorophenyl)pyrrole (94 mg) as amorphous powder.

NMR (CDCl$_3$, δ): 1.05 (9H, s), 2.79 (3H, s), 4.19 (2H, d, J=6 Hz), 4.94 (2H, s), 5.38 (1H, br peak), 6.23–6.30 (2H, m), 6.65 (1H, d, J=2 Hz), 7.17 (1H, d, J=8 Hz), 7.25 (1H, d, J=6 Hz), 7.34–7.49 (6H, m), 7.70–7.78 (4H, m)

(2) 2-Acetamidomethyl-1-(2,4-dichloro-3-hydroxymethylphenyl)-pyrrole was obtained according to a similar manner to that of Example 13-(5).

NMR (CDCl$_3$, δ): 1.81 (3H, s), 2.65 (1H, br s), 4.25 (2H, t, J=6 Hz), 5.01 (2H, br s), 5.44 (1H, br s), 6.23–6.31 (2H, m), 6.89 (1H, br s), 7.25 (1H, d, J=8 Hz), 7.44 (1H, d, J=8 Hz)

(3) To a mixture of 2-acetamidomethyl-1-(2,4-dichloro-3-hydroxymethylphenyl)pyrrole (51 mg) and triethylamine (19.8 mg) in dichloromethane (2 ml) was added methanesulfonyl chloride (20.5 mg) under nitrogen atmosphere in ice-methanol bath, and the mixture was stirred for 2 hours at the same temperature. The reaction mixture was poured into water and extracted with chloroform. The extract was washed with water, saturated sodium bicarbonate solution and brine, dried over magnesium sulfate and evaporated in vacuo to give 2-acetamidomethyl-1-[2,4-dichloro-3-(methanesulfonyloxymethyl)-phenyl]pyrrole (64 mg) as oil.

NMR (CDCl$_3$, δ): 1.84 (3H, s), 3.12 (3H, s), 4.18–4.23 (2H, m), 5.58 (2H, s), 6.25–6.31 (2H, m), 6.63–6.69 (1H, m), 7.38 (1H, d, J=8 Hz), 7.50 (1H, d, J=8 Hz)

(4) 2-Acetamidomethyl-1-[2,4-dichloro-3-[2-methyl-4-(2-pyridylmethoxy)quinolin-8-yloxymethyl]phenyl]pyrrole is obtained according to a similar manner to that of Example 1-(2).

Example 18

(1) 1-(3-tert-Butyldiphenylsilyloxymethyl-2,4-dichlorophenyl)-2-[4-[N-(2-pyridylmethyl)carbamoyl]-cinnamoylaminomethyl]pyrrole was obtained from 2-aminomethyl- 1-(3-tert-butyldiphenylsilyloxymethyl-2,4-dichlorophenyl)-pyrrole and 4-(N-(2-pyridylmethyl) carbamoyl]cinnamic acid according to a similar manner to that of Example 13-(4).

NMR (CDCl$_3$, δ): 4.33 (2H, d, J=5 Hz), 4.77 (2H, d, J=5 Hz), 4.90 (2H, s), 5.60 (1H, t-like), 6.19–6.34 (3H, m), 6.65–6.70 (1H, m), 7.20–7.80 (21H, m), 8.58 (1H, d, J=6 Hz)

(2) 1-(2,4-Dichloro-3-hydroxymethylphenyl)-2-[4-[N-(2-pyridylmethyl)carbamoyl]cinnamoylaminomethyl]pyrrole was obtained according to a similar manner to that of Example 13-(5).

NMR (DMSO-d$_6$, δ): 4.06 (1H, dd, J=5, 15 Hz), 4.20 (1H, dd, J=5, 15 Hz), 4.58 (2H, d, J=7 Hz), 4.71 (2H, d, J=5 Hz), 5.30 (1H, t, J=7 Hz), 6.18–6.24 (2H, m), 6.65 (1H, d, J=16

Hz), 6.74–6.79 (1H, m), 7.28 (1H, dd, J=6, 8 Hz), 7.30–7.40 (2H, m), 7.45 (1H, d, J=8 Hz), 7.57 (1H, d, J=8 Hz), 7.63 (2H, d, J=8 Hz), 7.76 (1H, t, J=8 Hz), 7.95 (2H, d, J=8 Hz), 8.30 (1H, t, J=6 Hz), 8.51 (1H, d, J=6 Hz), 9.16 (1H, t, J=6 Hz)

(3) 1-(2,4-Dichloro-3-chloromethylphenyl)-2-[4-[N-(2-pyridylmethyl)carbamoyl]cinnamoylaminomethyl]pyrrole was obtained according to a similar manner to that of Example 13-(6).

NMR (CDCl$_3$, δ): 4.27–4.48 (2H, m), 4.77 (2H, d, J=5 Hz), 4.85 (2H, s), 5.61 (1H, br peak), 6.24–6.36 (3H, m), 6.67–6.72 (1H, m), 7.20–7.28 (1H, m), 7.33 (2H, d, J=8 Hz), 7.44–7.57 (4H, m), 7.57–7.75 (2H, m), 7.88 (2H, d, J=8 Hz), 8.59 (1H, d, J=6 Hz)

(4) 1-[2,4-Dichloro-3-[2-methyl-4-(2-pyridylmethoxy) quinolin-8-yloxymethyl]phenyl]-2-[4-[N-(2-pyridylmethyl) carbamoyl]-cinnamoylaminomethyl]pyrrole is obtained according to a similar to that of Example 1-(2).

Example 19

(1) To a mixture of 3-aminophenylboronic acid hemisulfate (472 mg) in toluene (11 ml) were added tetrakis(triphenylphosphine)palladium(O) (64 mg), 2M sodium carbonate solution (5.5 ml), methanol (2.8 ml) and 1-tert-butyldiphenylsilyloxymethyl-2,6-dimethyl-3-bromobenzene (1.0 g) at ambient temperature, and the mixture was heated at 80° C. After 5 hours, the cooled reaction mixture was extracted with chloroform and the organic layer was washed with aqueous sodium bicarbonate solution and brine. The organic layer was dried over magnesium sulfate and evaporated in vacuo. The residue was purified by flash silica gel chromatography eluted with n-hexane-ethyl acetate to give 3-(3-aminophenyl)-1-tert-butyldiphenylsilyloxymetyl-2,6-dimethylbenzene (350 mg) as pale yellow oil.

NMR (CDCl$_3$, δ): 1.05 (9H, s), 2.14 (3H, s), 2.26 (3H, s), 3.67 (2H, br s), 4.77 (2H, s), 6.56–6.80 (3H, m), 7.00 (1H, d, J=8 Hz), 7.06 (1H, d, J=8 Hz), 7.16 (1H, t, J=8 Hz), 7.32–7.48 (6H, m), 7.70 (4H, br d, J=8 Hz)

(2) 3-(3-Acetamidophenyl)-1-tert-butyldiphenylsilyloxymethyl-2,6-dimethylbenzene was obtained according to a similar manner to that of Example 17-(1).

NMR (CDCl$_3$, δ): 1.05 (9H, s), 2.14 (3H, s), 2.19 (3H, s), 2.27 (3H, s), 4.78 (2H, s), 6.98–7.08 (3H, m), 7.13 (1H, br s), 7.27–7.48 (8H, m), 7.57 (1H, br d, J=8 Hz), 7.70 (4H, br d, J=8 Hz), (3) 3-(3-Acetamidophenyl)-1-hydroxymethyl-2,6-dimethylbenzene was obtained according to a similar manner to that of Example 13-(5).

NMR (CDCl$_3$, δ): 2.17 (3H, s), 2.31 (3H, s), 2.49 (3H, s), 4.81 (2H, br s), 7.00 (1H, br d, J=8 Hz), 7.05–7.10 (2H, m), 7.19 (1H, br s), 7.30–7.40 (2H, m), 7.51 (1H, br d, J=8 Hz)

(4) 3-(3-Acetamidophenyl)-1-chloromethyl-2,6-dimethylbenzene was obtained according to a similar manner to that of Example 13-(6).

NMR (CDCl$_3$, δ): 2.18 (3H, s), 2.32 (3H, s), 2.49 (3H, s), 4.74 (2H, s), 7.01 (1H, br d, J=8 Hz), 7.05–7.15 (2H, m), 7.20 (1H, br s), 7.30–7.43 (2H, m), 7.52 (1H, br d, J=8 Hz)

(5) 8-[3-(3-Acetamidophenyl)-2,6-dimethylbenzyloxy]-2-methyl-4-(2-pyridylmethoxy)quinoline is obtained according to a similar manner to that of Example 1-(2).

Example 20

(1) 1-tert-Butyldiphenylsilyloxymethyl-2,6-dimethyl-3-[3-[4-(methylcarbamoyl)cinnamoylamino]phenyl]benzene was obtained from 3-(3-aminophenyl)-1-tert-butyldiphenylsilyloxymethyl-2,6-dimethylbenzene and 4-(methylcarbamoyl)cinnamic acid according to a similar manner to that of Example 13-(4).

mp: 245–247° C. NMR (DMSO-d$_6$, δ): 1.01 (9H, s), 2.12 (3H, s), 2.21 (3H, s), 2.79 (3H, d, J=5 Hz), 4.79 (2H, s), 6.88–6.98 (2H, m), 7.01–7.11 (2H, m), 7.30–7.52 (7H, m), 7.59–7.75 (11H, m), 7.90 (2H, d, J=8 Hz), 8.51 (1H, br d, J=5 Hz)

(2) 1-Hydroxymethyl-2,6-dimethyl-3-[3-[4-(methylcarbamoyl)-cinnamoylamino]phenyl]benzene was obtained according to a similar manner to that of Example 13-(5).

mp: 272–277° C. NMR (DMSO-d$_6$, δ): 2.28 (3H, s), 2.40 (3H, s), 2.80 (3H, d, J=5 Hz), 4.57 (2H ,d, J=6 Hz), 4.78 (1H, t, J=6 Hz), 6.87–7.10 (4H, m), 7.38 (1H, t, J=8 Hz), 7.57–7.74 (5H, m), 7.89 (2H, d, J=8 Hz), 8.50 (1H, br d, J=5 Hz)

(3) 1-Chloromethyl-2,6-dimethyl-3-[3-[4-(methylcarbamoyl)-cinnamoylamino]phenyl]benzene was obtained according to a similar manner to that of Example 13-(6).

mp: 236.2–243.8° C. NMR (DMSO-d$_6$, δ): 2.30 (3H, s), 2.44 (3H, s), 2.79 (3H, d, J=5 Hz), 4.88 (2H, s), 4.78 (1H, t, J=6 Hz), 6.90 (1H, d, J=15 Hz), 6.99 (1H, br d, J=8 Hz), 7.09–7.21 (2H, m), 7.40 (1H, t, J=8 Hz), 7.58–7.74 (5H, m), 7.89 (2H, d, J=8 Hz), 8.50 (1H, br d, J=5 Hz)

(4) 2-Methyl-8-[2,6-dimethyl-3-[3-[4-(methylcarbamoyl)-cinnamoylamino]phenyl]benzyloxy]-4-(2-pyridylmethoxy)-quinoline is obtained according to a similar manner to that of Example 1-(2).

Example 21

(1) To a solution of 3-bromo-1-tert-butyldiphenylsilyloxymethyl-2,6-dimethylbenzene (1.65 g) in anhydrous tetrahydrofuran (15 ml) was added 1.6N solution of n-butyllithium in n-hexane (2.6 ml) dropwise in a dry-ice acetone bath, and the mixture was stirred at the same temperature for 1 hour. To this mixture was added a solution of zinc chloride (500 mg) in tetrahydrofuran (10 ml) dropwise under dry-ice acetone cooling. The dry-ice acetone bath was removed, and the reaction mixture was stirred at ambient temperature for 1 hour. This mixture was added to a solution of 3-bromo-2-cyanothiophene (684 mg) and tetrakis(triphenylphosphine)palladium (O) (210 mg) in tetrahydrofuran (2 ml) dropwise at ambient temperature. The reaction mixture was stirred at the same temperature for 30 minutes and stood overnight in the dark. The mxiture was diluted with ethyl acetate, washed with 1N hydrochloric acid and water, dried over magnesium sulfate and evaporated in vacuo. The residue was purified by a silica gel column chromatography (n-hexane-ethyl acetate) to give 3-(3-tert-butyldiphenylsilyloxymethyl-2,4-dimethylphenyl)-2-cyanothiophene (508 mg).

NMR (CDCl$_3$, δ): 1.04 (9H, s), 2.13 (3H, s), 2.25 (3H, s), 4.76 (2H, s), 7.00–7.08 (2H, m), 7.13 (1H, d, J=8 Hz), 7.32–7.48 (6H, m), 7.56 (1H, d, J=6 Hz), 7.69 (4H, d-like)

(2) A mixture of 3-(3-tert-butyldiphenylsilyloxymethyl-2,4-dimethylphenyl)-2-cyanothiophene (471 mg) and 1M borane-tetrahydrofuran complex (3 ml) was stirred for 30 minutes at 0° C. under nitrogen atmosphere and allowed to stand at ambient temperature overnight. To the mixture was added 4N hydrochloric acid (1.5 ml) under ice-cooling, and the mixture was stirred for 1 hour. The mixture was partitioned between ethyl acetate and water, and the separated organic layer was washed with water and brine, dried over magnesium sulfate and evaporated in vacuo. The residue was purified by silica gel column chromatography (chloroform:methanol =50:1, V/V) to give 2-aminomethyl-3-(3-tert-butyldiphenylsilyloxymethyl-2,4-dimethylphenyl) thiophene (415 mg) as oil.

NMR (CDCl$_3$, δ): 1.05 (9H, s), 2.02 (3H, s), 2.27 (3H, s), 3.78 (2H, s), 4.76 (2H, s), 6.83 (1H, d, J=6 Hz), 7.00 (2H, s-like), 7.20 (1H, d, J=6 Hz), 7.30–7.48 (6H, m), 7.63–7.75 (4H, m)

(3) 3-(3-tert-Butyldiphenylsilyloxymethyl-2,4-dimethylphenyl)-2-[4-(methylcarbamoyl)cinnamoylaminomethyl]-thiophene was obtained according to a similar manner to that of Example 13-(4).

NMR (CDCl$_3$, δ): 1.05 (9H, s), 2.05 (3H, s), 2.28 (3H, s), 3.02 (3H, d, J=6 Hz), 4.49 (2H, br peak), 4.77 (2H, s), 6.00 (1H, br peak), 6.29 (1H, br peak), 6.35 (1H, d, J=16 Hz), 6.85 (1H, d, J=6 Hz), 7.02 (2H, s-like), 7.25 (1H, d, J=8 Hz), 7.33–7.90 (15H, m)

(4) 3-(2,4-Dimethyl-3-hydroxymethylphenyl)-2-[4-(methylcarbamoyl)cinnamoylaminomethyl]thiophene was obtained according to a similar manner to that of Example 13-(5).

NMR (CDCl$_3$-CD$_3$OD, δ): 1.94 (1H, s), 2.23 (3H, s), 2.44 (3H, s), 3.00 (3H, s), 4.50 (2H, s), 4.80 (2H, s), 6.31 (1H, d, J=16 Hz), 6.41 (1H, br peak), 6.88 (1H, d, J=6 Hz), 7.02 (1H, d, J=8 Hz), 7.08 (1H, d, J=8 Hz), 7.23–7.30 (1H, m), 7.50 (2H, d, J=8 Hz), 7.55 (1H, d, J=16 Hz), 7.74 (2H, d, J=8 Hz)

(5) 3-(3-Chloromethyl-2,4-dimethylphenyl)-2-[4-(methylcarbamoyl)cinnamoylaminomethyl]thiophene was obtained according to a similar manner to that of Example 13-(6).

NMR (CDCl$_3$, δ): 2.24 (3H, s), 2.47 (3H, s), 3.02 (3H, d, J=6 Hz), 4.53 (2H, br s), 4.73 (2H, s), 5.73 (1H, br peak), 6.10 (1H, br peak), 6.34 (1H, d, J=16 Hz), 6.88 (1H, d, J=6 Hz), 7.04–7.13 (2H, m), 7.22–7.30 (1H, m), 7.52 (2H, d, J=8 Hz), 7.61 (1H, d, J=16 Hz), 7.74 (1H, d, J=8 Hz)

(6) 3-[2,4-Dimethyl-3-[2-methyl-4-(2-pyridylmethoxy)quinolin-8-yloxymethyl]phenyl]-2-[4-(methylcarbamoyl)cinnamoylamino-methyl]thiophene is obtained according to a similar manner to that of Example 1-(2).

Example 22

(1) 2-Acetamidomethyl-3-(3-tert-butyldiphenylsilyloxymethyl-2,4-dimethylphenyl)thiophene was obtained from 2-aminomethyl-3-(3-tert-butyldiphenylsilyloxymethyl-2,4-dimethylphenyl)-thiophene and acetic anhydride according to a similar manner to that of Example 17-(1).

NMR (CDCl$_3$, δ): 1.05 (9H, s), 1.91 (3H, s), 2.00 (3H, s), 2.26 (3H, s), 4.35 (2H, br s), 4.75 (2H, s), 5.50 (1H, br s), 6.83 (1H, d, J-=6 Hz), 6.96 (1H, d, J=7.5 Hz), 7.02 (1H, d, J=7.5 Hz), 7.23 (1H, d, J=6 Hz), 7.31–7.49 (6H, m), 7.69 (4H, d-like)

(2) 2-Acetamidomethyl-3-(2,4-dimethyl-3-hydroxymethylphenyl)-thiophene was obtained according to a similar manner to that of Example 13-(5).

NMR (CDCl$_3$, δ): 1.66 (1H, t-like), 1.89 (3H, s), 2.23 (3H, s), 2.49 (3H, s), 4.39 (2H, d, J=6 Hz), 4.81 (2H, s), 5.53 (1H, br s), 6.88 (1H, d, J=6 Hz), 7.00 (1H, d, J=8 Hz), 7.09 (1H, d, J=8 Hz), 7.22–7.28 (1H, m)

(3) 2-Acetamidomethyl-3-(3-methanesulfonyloxymethyl-2,4-dimethylphenyl)thiophene was obtained according to a similar manner to that of Example 17-(3).

NMR (CDCl$_3$, δ): 1.93 (3H, s), 2.22 (3H, s), 2.47 (3H, s), 3.69 (3H, s), 4.37 (2H, br peak), 4.73 (2H, s), 5.53 (1H, br peak), 6.86 (1H, d, J=5 Hz), 7.03 (1H, d, J=8 Hz), 7.10 (1H, d, J=8 Hz), 7.25 (1H, d, J=5 Hz)

(4) 2-Acetamidomethyl-3-[3-[2-methyl-4-(2-pyridylmethoxy)quinolin-8-yloxymethyl]-2,4-dimethylphenyl]thiophene is obtained according to a similar manner to that of Example 1-(2).

Example 23

(1) 1-tert-Butyldiphenylsilyloxymethyl-2,6-dimethyl-3-((Z)-1-methyl-3-trityloxy-1-propenyl)benzene was obtained from 3-bromo-1-tert-butyldiphenylsilyloxymethyl-2,6-dimethylbenzene and 2-iodo-4-trityloxy-2-butene according to a similar manner to that of Example 21-(1).

NMR (CDCl$_3$, δ): 1.00 (9H, s), 1.92 (3H, br s), 1.99 (3H, s), 2.19 (3H, s), 3.26–3.34 (2H, m), 4.62 (1H, br s), 4.66 (1H, br s), 5.63 (1H, br t, J=7 Hz), 6.77 (1H, d, J=8 Hz), 6.85 (1H, d, J=8 Hz), 7.08–7.20 (8H, m), 7.22–7.49 (13H, m), 7.65 (4H, d, J=8 Hz)

(2) A solution of 1-tert-butyldiphenylsilyloxymethyl-2,6-dimethyl-3-((Z)-1-methyl-3-trityloxy-1-propenyl)benzene (500 mg) in acetic acid (5 ml) was heated at 60° C. for 10 hours. The cooled reaction mixture was concentrated in vacuo and ethyl acetate was added thereto. The mixture was washed with aqueous sodium bicarbonate solution, water and brine, dried over magnesium sulfate and evaporated in vacua. The residue was purified by flash silica gel chromatography eluted with n-hexane-ethyl acetate to give 1-tert-butyldiphenylsilyloxymethyl-2,6-dimethyl-3-((Z)-3-hydroxy-1-methyl-1-propenyl)benzene (92 mg) as colorless oil.

NMR (CDCl$_3$, δ): 1.02 (9H, s), 1.95 (3H, s), 2.09 (3H, s), 2.21 (3H, s), 3.77–3.85 (2H, m), 4.73 (2H, s), 5.70 (1H, br t, J=7 Hz), 6.83 (1H, d, J=8 Hz), 6.95 (1H, br d, J=8 Hz), 7.32–7.47 (6H, m), 7.68 (4H, d, J=8 Hz)

(3) To a mixture of 1-tert-butyldiphenylsilyloxymethyl-2,6-dimethyl-3-((Z)-3-hydroxy-1-methyl-1-propenyl)benzene (120 mg) and triethylamine (32.8 mg) in dichloromethane (1.2 ml) was dropwise added methanesulfonyl chloride (34 mg) under ice-cooling, and the mixture was stirred for 30 minutes at the same temperature. The mixture was washed with water, saturated sodium bicarbonate solution and brine, dried over magnesium sulfate and evaporated in vacua to give 1-tert-butyldiphenylsilyloxymethyl-2,6-dimethyl-3-((Z)-3-methanesulfonyloxy-1-methyl-1-propenyl)benzene (132 mg) as colorless oil.

NMR (CDCl$_3$, δ): 1.04 (9H, s), 2.00 (3H, s), 2.09 (3H, s), 2.21 (3H, s), 2.81 (3H, s), 4.39 (2H, br d, J=7 Hz), 4.72 (2H, s), 5.71 (1H, br t, J=7 Hz), 6.82 (1H, d, J=8 Hz), 6.97 (1H, br d, J=8 Hz), 7.32–7.48 (6H, m)r, 7.64–7.71 (4H, m)

(4) To a solution of 1-tert-butyldiphenylsilyloxymethyl-2,6-dimethyl-3-((Z)-3-methanesulfonyloxy-1-methyl-1-propenyl)benzene (132 mg) in N,N-dimethylformamide was added potassium phthalimide (55 mg) at ambient temperature under nitrogen atmosphere, and the mixture was stirred at the same temperature overnight. The mixture was poured into water and extracted with ethyl acetate. The organic layer was washed with water, dried over magnesium sulfate and evaporated in vacuo. The residue was purified by preparative thin layer chromatography (n-hexane:ethyl acetate =4:1, V/V) to give 1-tert-butyldiphenylsilyloxymethyl-2,6-dimethyl-3-((z)-1-methyl-3-phthalimido-1-propenyl)benzene (99 mg) as colorless oil.

NMR (CDCl$_3$, δ): 1.04 (9H, s), 1.91 (3H, br s), 2.15 (3H, s), 2.21 (3H, s), 3.99 (2H, br d, J=7 Hz), 4.73 (2H, s), 5.49 (1H, br t, J=7 Hz), 6.95 (1H, d, J=8 Hz), 7.00 (1H, d, J=8 Hz), 7.32–7.47 (6H, m), 7.61–7.74 (6H, m), 7.75–7.81 (2H, m)

(5) To a suspension of 1-tert-butyldiphenylsilyloxymethyl-2,6-dimethyl-3-((Z)-1-methyl-3-phthalimido-1-propenyl)benzene (94 mg) in ethanol (1 ml) was added hydrazine monohydrate (16.4 mg), and the mixture was refluxed for 1 hour. After cooling, the insoluble material was filtered off, and the filtrate was concentrated in vacuo. To the residue was added dichloromethane, and the insoluble material was filtered off. The filtrate was concentrated in vacuo to give 3-((Z)-3-amino-1-methyl-1-propenyl)-1-tert-butyldiphenylsilyloxy-methyl-2,6-dimethylbenzene (66 mg) as pale yellow amorphous.

NMR (CDCl$_3$, δ): 1.03 (9H, s), 1.91 (3H, br s), 2.09 (3H, s), 2.20 (3H, s), 2.93 (2H, br d, J=7 Hz), 4.73 (2H, s), 5.58 (1H, br t, J=7 Hz), 6.83 (1H, d, J=8 Hz), 6.95 (1H, br d, J=8 Hz), 7.31–7.48 (6H, m), 7.63–7.72 (6H, m)

(6) 3-[(Z)-3-[(E)-3-[6-(Acetamido)pyridin-3-yl] acryloylamino]-1-methyl-1-propenyl]-1-tert-butyldiphenylsilyloxymethyl-2,6-dimethylbenzene was obtained according to a similar manner to that of Example 13-(4).

NMR (CDCl$_3$, δ): 1.02 (9H, s), 1.93 (3H, br s), 2.09 (3H, s), 2.21 (3H, s), 2.23 (3H, s), 3.50–3.83 (2H, m), 4.72 (2H, s), 5.40 (1H, br s), 5.59 (1H, br t, J=7 Hz), 6.25 (1H, d, J=15 Hz), 6.85 (1H, d, J=8 Hz), 6.98 (1H, br d, J=8 Hz), 7.32–7.46 (6H, m), 7.52 (1H, d, J=15 Hz), 7.68 (4H, d, J=8 Hz), 7.80 (1H, dd, J=8, 3 Hz), 7.97 (1H, br s), 8.20 (1H, br d, J=8 Hz), 8.32 (1H, br s)

(7) 3-[(Z)-3-[(E)-3-[6-(Acetamido)pyridin-3-yl] acryloylamino]-1-methyl-1-propenyl]-1-hydroxymethyl-2,6-dlmethylbenzene was obtained according to a similar manner to that of Example 13-(5).

mp: 160–165° C. NMR (CDCl$_3$, δ): 1.96 (3H, br s), 2.21 (3H, s), 2.30 (3H, s), 2.41 (3H, s), 3.54–3.80 (2H, m), 4.77 (2H, d, J=δHz), 5.50 (1H, br t, J=5 Hz), 5.62 (1H, br t, J=7 Hz), 6.26 (1H, d, J=15 Hz), 6.88 (1H, d, J=8 Hz), 7.03 (1H, br d, J=8 Hz), 7.50 (1H, d, J=15 Hz), 7.80 (1H, dd, J=8, 3 Hz), 8.02 (1H, br s), 8.20 (1H, br d, J=8 Hz), 8.31 (1H, br s)

(8) 3-[(Z)-3-[(E)-3-[6-(Acetamido)pyridin-3-yl] acryloylamino]-1-methyl-1-propenyl]-1-chloromethyl-2,6-dimethylbenzene was obtained according to a similar manner to that of Example 13-(6)

NMR (CDCl$_3$, δ): 1.96 (3H, br s), 2.21 (3H, s), 2.31 (3H, s), 2.41 (3H, s), 3.53–3.82 (2H, m), 4.69 (2H, s), 5.47 (1H, br s), 5.63 (1H, br t, J=7 Hz), 6.28 (1H, d, J=15 Hz), 6.91 (1H, d, J=8 Hz), 7.05 (1H, br d, J=8 Hz), 7.51 (1H, d, J=15 Hz), 7.80 (1H, dd, J=B, 3 Hz), 7.99 (1H, br s), 8.20 (1H, br d, J=8 Hz), 8.33 (1H, br s)

(9) 8-[3-[(Z)-3-[(E)-3-[6-(Acetamido)pyridin-3-yl] acryloylamino]-1-methyl-1-propenyl]-2,6-dimethylbenzyloxy]-2-methyl-4-(2-pyridylmethoxy) quinoline was obtained according to a similar manner to that of Example 1-(2).

Example 24

(1) To a mixture of 2-acetamido-5-bromopyridine (240 mg), tri-n-butylamine (456 mg), palladium(II) acetate (0.13 mg) and triphenylphosphine (1.5 mg) in xylene (0.48 ml) was dropwise added acrylic acid (97 mg) at 150° C., and the mixture was stirred for 7 hours at the same temperature. After cooling the mixture, water was added thereto, and the mixture was adjusted to pH4 with hydrochloric acid. The precipitate was collected by filtration, washed with xylene and water, and dried to give (E)-3-(6-acetamidopyridin-3-yl)acrylic acid (173 mg) as yellow crystals.

mp: 291–292° C. NMR (DMSO-d$_6$, δ): 2.10 (3H, s), 6.55 (1H, d, J=16 Hz), 7.58 (1H, d, J=16 Hz), 8.07–8.21 (2H), 8.59 (1H, br s)

(2) 2-[(E)-3-(6-Acetamidopyridin-3-yl) acryloylaminomethyl]-1-(3-tert-butyldiphenylsilyloxymethyl-2,4-dichlorophenyl)pyrrole was obtained from 2-aminomethyl-1-(3-tert-butyldiphenylsilyloxymethyl-2,4-dichlorophenyl)pyrrole and (E)-3-(6-acetamidopyridin-3-yl)acrylic acid according to a similar manner to that of Example 13-(4).

NMR (DMSO-d$_6$, δ): 0.98 (9H, s), 2.10 (2H, s), 2.15 (1H, s), 4.03 (1H, dd, J=15, 6 Hz), 4.22 (1H, dd, J=15, 6 Hz), 4.89 (2H, s), 6.16–6.22 (2H), 6.52 (1H, d, J=15 Hz), 6.76 (1H, d, J=2 Hz), 7.17–8.49 (17H), 8.80 (1H, br s)

(3) 2-[(E)-3-(6-Acetamidopyridin-3-yl) acryloylaminomethyl]-1-(2,4-dichloro-3-hydroxymethylphenyl)pyrrole was obtained according to a similar manner to that of Example 13-(5).

NMR (DMSO-d$_6$, δ): 2.12 (3H, s), 4.04 (1H, dd, J=15, 6 Hz), 4.19 (1H, dd, J=15, 6 Hz), 4.72 (2H, d, J=6 Hz), 5.30 (1H, t, J=6 Hz), 6.17–6.22 (2H), 6.56 (1H, d, J=15 Hz), 6.76 (1H, d, J=3 Hz), 7,29 (1H, d, J=15 Hz), 7.45 (1H, d, J=8 Hz), 7.57 (1H, d, J=8 Hz), 7.89–8.26 (4H), 8.43 (1H, br s)

(4) 2-[(E)-3-(6-Acetamidopyridin-3-yl) acryloylaminomethyl]-1-[2,4-dichloro-3-(methanesulfonyloxymethyl)phenyl]pyrrole was obtained according to a similar manner to that of Example 17-(3).

NMR (CDCl$_3$, δ): 2.23 (3H, s), 3.08 (3H, s), 4.29 (1H, dd, J=15, 6 Hz), 4.41 (1H, dd, J=15, 6 Hz), 5.49–5.70 (3H), 6.25 (1H, d, J=15 Hz), 6.29–6.36(2H), 6.68 (1H, d, J=2 Hz) 7.22–7.50 (3H), 7.82 (1H, dd, J=8, 2 Hz), 8.22 (1H, d, J=8 Hz), 8.35 (1H, d, J=2 Hz)

(5) 2-[(E)-3-(6-Acetamidopyridin-3-yl) acryloylaminomethyl]-1-[2,4-dichloro-3-[2-methyl-4-(2-pyridylmethoxy)quinolin-8-yloxymethyl]phenyl]pyrrole is obtained according to a similar manner to that of Example 1-(2).

Example 25

(1) 1-[2,4-Dichloro-3-(2-methoxy-1H-benzimidazol-4-yloxymethyl)phenyl]-2-[4-(methylcarbamoyl) cinnamoylamino-methyl]pyrrole is obtained by reacting 1-(2,4-dichloro-3-chloromthlphenyl)- 2-[4-(methylcarbamoyl)cinnamoylamino-methyl]pyrrole with 4-hydroxy-2-methoxy-1H-benzimidazole according to a similar manner to that of Example 1-(2).

(2) 1-[2,4-Dichloro-3-[2-methoxy-1-(2-pyridylmethoxy)-1H-benzimidazol-4-yloxymethyl]phenyl]-2-[4-(methylcarbamoyl)-cinnamoylaminomethyl]pyrrole is obtained by reacting 1-[2,4-dichloro-3-(2-methoxy-1H-benzimidazol-4-yloxymethyl)phenyl]-2-[4-(methylcarbamoyl)cinnamoylaminomethyl]pyrrole with 2-chloromethylpyridine according to a similar manner to that of Example 9.

We claim:
1. A compound of the formula:

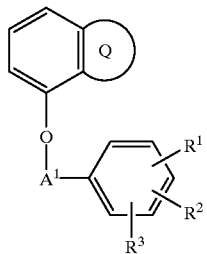

or its pharmaceutical acceptable salt, wherein

is a group of the formula:

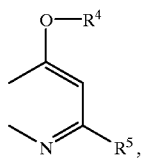

in which
R$^4$ is heterocyclic(lower)alkyl, and
R$^5$ is lower alkyl,
R$^1$ is hydrogen, lower alkyl or halogen,
R$^2$ is lower alkyl or halogen,
R$^3$ is amino mono- or di-substituted with substituent(s) selected from the group consisting of lower alkyl and acyl, or a group of the formula:

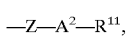

in which
R$^{11}$ is amino or acylamino,
A$^2$ is lower alkylene or a single bond, and
Z is lower alkenylene or a group of the formula:

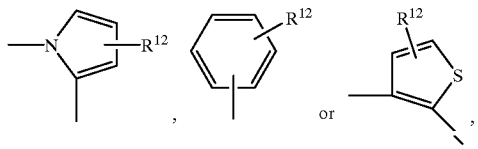

in which
R$^{12}$ is hydrogen or halogen,
and
A$^1$ is lower alkylene.
2. A compound of claim 1, wherein
R$^4$ is pyridyl(lower)alkyl, and
A$^1$ is methylene.
3. A compound of claim 2, wherein
R$^3$ is a group of the formula:

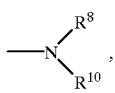

wherein
R$^8$ is hydrogen or lower alkyl, and
R$^{10}$ is a group of the formula:

—(AA)—CO—Y—R$^9$, in which
R$^9$ is aryl or a heterocyclic group, each of which may be substituted with substituent(s) selected from the group consisting of amino, acyl, acylamino, lower alkyl, lower alkoxy, heterocyclic(lower)alkenyl and a heterocyclic group optionally substituted with oxo,
(AA) is amino acid residue, and
Y is lower alkenylene or NH,
or a group of the formula:

wherein
R$^{11}$ is amino, lower alkanoylamino or a group of the formula:

—NH—CO—Y—R$^9$ in which R$^9$ and Y are each as defined above,
A$^2$ is lower alkylene or a single bond, and
Z is lower alkenylene or a group of the formula:

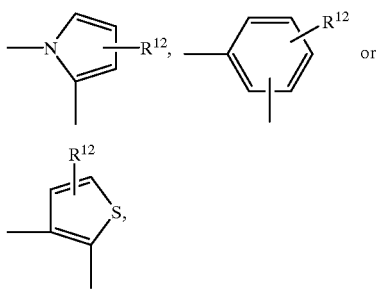

in which
R$^{12}$ is hydrogen or halogen.
4. A compound of claim 3, wherein
R$^3$ is a group of the formula:

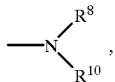

wherein
R$^8$ is hydrogen or lower alkyl, and
R$^{10}$ is a group of the formula:

—(AA)—CO—Y—R$^9$, in which
R$^9$ is phenyl or pyridyl, each of which may be substituted with substituent(s) selected from the group consisting of amino, lower alkoxycarbonyl, lower alkylcarbamoyl, pyridyl(lower)alkylcarbamoyl, pyridylcarbamoyl, lower alkanoylamino, pyridylcarbonylamino optionally substituted with lower alkyl, pyridyl(lower)alkanoylamino, lower alkyl, lower alkoxy, pyridyl(lower)alkenyl and oxopyrrolidinyl, (AA) is glycyl, and Y is lower alkenylene or NH.

5. A compound of claim 3, wherein $R^3$ is a group of the formula:

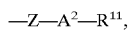
—Z—A²—R¹¹, wherein $R^{11}$ is amino, lower alkanoylamino or a group of the formula:

—NH—CO—Y—R⁹ in which $R^9$ is phenyl or pyridyl, each of which may be substituted with substituent(s) selected from the group consisting of amino, lower alkoxycarbonyl, lower alkylcarbamoyl, pyridyl(lower)alkylcarbamoyl, pyridylcarbamoyl, lower alkanoylamino, pyridylcarbonylamino optionally substituted with lower alkyl, pyridyl(lower)alkanoylamino, lower alkyl, lower alkoxy, pyridyl(lower)alkenyl and oxopyrrolidinyl, and Y is lower alkenylene or NH, $A^2$ is lower alkylene or a single bond, and Z is lower alkenylene or a group of the formula:

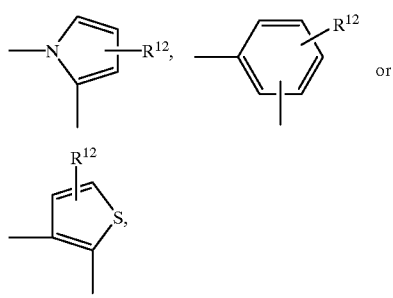

in which $R^{12}$ is hydrogen or halogen.

6. A compound according to claim 1, which is 8-[2,6-dichloro-3-[N-[4-(methylcarbamoyl)cinnamoylglycyl]-N-methylamino]benzyloxy]-2-methyl-4-(2-pyridylmethoxy)quinoline.

7. A process for preparing a compound of the formula:

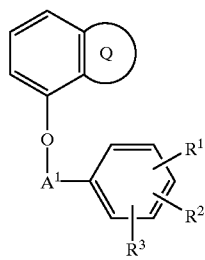

wherein

is a group of the formula:

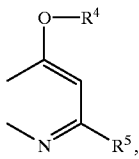

in which $R^4$ is heterocyclic(lower)alkyl, and $R^5$ is lower alkyl, $R^1$ is hydrogen, lower alkyl or halogen, $R^2$ is lower alkyl or halogen, $R^3$ is amino mono- or di-substituted with substituent(s) selected from the group consisting of lower alkyl and acyl, or a group of the formula:

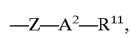
—Z—A²—R¹¹, in which $R^{11}$ is amino or acylamino, $A^2$ is lower alkylene or a single bond, and Z is lower alkenylene or a group of the formula:

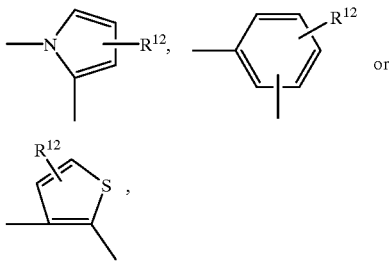

in which $R^{12}$ is hydrogen or halogen, and $A^1$ is lower alkylene, or its salt, which comprises a) reacting a compound of the formula:

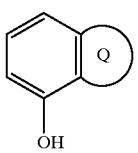

wherein

is as defined above, or its salt with a compound of the formula:

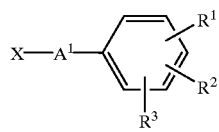

wherein X is a leaving group, and
R$^1$, R$^2$, R$^3$ and A$^1$ are each as defined above, or its salt to give a compound of the formula:

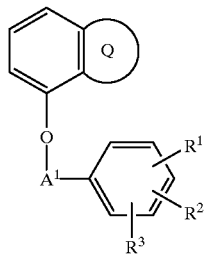

wherein R$^1$, R$^2$ R$^3$, A$^1$ and

are each as defined above,
or its salt, or
b) reacting a compound of the formula:

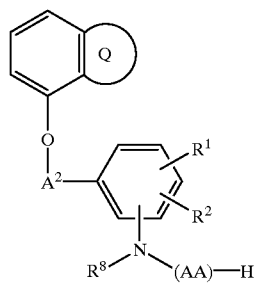

wherein R$^8$ is hydrogen or lower alkyl,
(AA) is amino acid residue, and R$^1$, R$^2$, A$^1$ and

are each as defined above,
or its salt with a compound of the formula:

R$^9$—Y—COOH wherein R$^9$ is aryl or a heterocyclic group, each of which may be substituted with substituent(s) selected from the group consisting of amino, acyl, acylamino, lower alkyl, lower alkoxy, heterocyclic(lower)alkenyl and a heterocyclic group optionally substituted with oxo, and Y is lower alkenylene or NH, or its reactive derivative at the carboxy group or a salt thereof to give a compound of the formula:

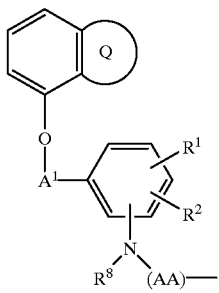

wherein R$^1$, R$^2$, R$^8$, R$^9$, A$^1$, (AA),

and
Y are each as defined above, or its salt.

8. A pharmaceutical composition comprising a compound of claim 1, as an active ingredient, in association with a pharmaceutically acceptable, substantially nontoxic carrier or excipient.

9. A method for the treatment of renal diseases, heart failure, hypertension, Ménière's disease, peripheral circulatory disorders, cerebral circulatory disorders, climacteric disturbance, retinochoroidal circulatory disorders, myocardial ischemia, myocardial infarction, postmyocardial infarction syndrome, angina pectoris, restenosis after percutaneous transluminal coronary angioplasty, hepatitis, liver cirrhosis, pancreatitis, ileus, diabetes, diabetic complications, male infertility or glaucoma, or for the increase of permeability of blood-brain barrier, which comprises administering a compound of claim 1 to human being or animals.

* * * * *